(12) United States Patent
Adams et al.

(10) Patent No.: US 7,232,452 B2
(45) Date of Patent: Jun. 19, 2007

(54) DEVICE TO CREATE PROXIMAL STASIS

(75) Inventors: Daniel O. Adams, Long Lake, MN (US); Richard S. Kusleika, Eden Prairie, MN (US); Kent D. Anderson, Champlin, MN (US)

(73) Assignee: ev3 Inc., Plymouth, MN (US)

( * ) Notice: Subject to any disclaimer, the term of this patent is extended or adjusted under 35 U.S.C. 154(b) by 397 days.

(21) Appl. No.: 10/194,355

(22) Filed: Jul. 12, 2002

(65) Prior Publication Data

US 2004/0010280 A1 Jan. 15, 2004

(51) Int. Cl.
*A61M 29/00* (2006.01)
(52) U.S. Cl. ...................................... 606/200
(58) Field of Classification Search ............ 606/194, 606/127, 200, 159; 604/500
See application file for complete search history.

(56) References Cited

U.S. PATENT DOCUMENTS

| | | |
|---|---|---|
| 3,000,380 A | 9/1961 | Doherty |
| 3,220,411 A | 11/1965 | Czorny |
| 3,262,449 A | 7/1966 | Pannier, Jr. et al. |
| 3,344,791 A | 10/1967 | Foderick |
| 3,583,391 A | 6/1971 | Cox et al. |
| 3,659,610 A | 5/1972 | Cimber |
| 3,703,174 A | 11/1972 | Smith |
| 3,777,743 A | 12/1973 | Binard |
| 3,877,429 A | 4/1975 | Rasumoff |
| 4,000,743 A | 1/1977 | Weaver |
| 4,023,559 A | 5/1977 | Gaskell |
| 4,198,981 A | 4/1980 | Sinnreich |
| 4,306,562 A | 12/1981 | Osborne |
| 4,552,554 A | 11/1985 | Gould et al. |
| 4,696,667 A | 9/1987 | Masch |
| 4,771,777 A | 9/1988 | Horzewski et al. |
| 4,781,682 A | 11/1988 | Patel |

(Continued)

FOREIGN PATENT DOCUMENTS

EP 0 427 429 A2 5/1991

(Continued)

OTHER PUBLICATIONS

International Search Report for counterpart PCT application, PCT/US03/20715 (8 pages).

(Continued)

*Primary Examiner*—Anhtuan T. Nguyen
*Assistant Examiner*—Elizabeth Houston
(74) *Attorney, Agent, or Firm*—Popovich, Wiles & O'Connell, P.A.

(57) ABSTRACT

A method and system of performing an intravascular procedure at a treatment site in a vessel of a patient. A device creates a seal to prevent the flow of blood during the treatment of vascular disease. A seal may be formed between the distal inside diameter of a sheath or catheter such as a guide catheter as well as within a vessel, such as an artery or vein. An elongated device having a distal portion extending from the catheter and having a fluid impermeable membrane disposed about at least the distal end of the device is used to seal the vessel. The system includes a device to occlude blood flow and a distal protection device to filter or remove embolic debris.

22 Claims, 19 Drawing Sheets

U.S. PATENT DOCUMENTS

| | | | |
|---|---|---|---|
| 4,794,928 A | 1/1989 | Kletschka | |
| 4,824,435 A | 4/1989 | Giesy et al. | |
| 4,886,500 A | 12/1989 | Lazarus | |
| 4,921,478 A | 5/1990 | Solano et al. | |
| 4,932,413 A | 6/1990 | Shockey et al. | |
| 4,946,440 A | 8/1990 | Hall | |
| 5,059,183 A | 10/1991 | Semrad | |
| 5,102,415 A * | 4/1992 | Guenther et al. | 606/159 |
| 5,120,323 A | 6/1992 | Shockey et al. | |
| 5,147,377 A | 9/1992 | Sahota | |
| 5,158,535 A | 10/1992 | Paul et al. | |
| 5,219,335 A | 6/1993 | Willard et al. | |
| 5,257,974 A | 11/1993 | Cox | |
| 5,290,247 A | 3/1994 | Crittenden | |
| 5,314,408 A | 5/1994 | Salmon et al. | |
| 5,338,300 A | 8/1994 | Cox | |
| 5,364,376 A | 11/1994 | Horzewski et al. | |
| 5,385,562 A | 1/1995 | Adams et al. | |
| 5,439,445 A | 8/1995 | Kontos | |
| 5,527,292 A | 6/1996 | Adams et al. | |
| 5,662,671 A * | 9/1997 | Barbut et al. | 606/170 |
| 5,738,667 A | 4/1998 | Solar | |
| 5,824,044 A | 10/1998 | Quiachon et al. | |
| 5,833,644 A * | 11/1998 | Zadno-Azizi et al. | 604/509 |
| 5,833,650 A * | 11/1998 | Imran | 604/509 |
| 5,843,027 A | 12/1998 | Stone et al. | |
| 6,022,319 A | 2/2000 | Willard et al. | |
| 6,022,336 A * | 2/2000 | Zadno-Azizi et al. | 604/101.05 |
| 6,066,100 A | 5/2000 | Willard et al. | |
| 6,139,573 A | 10/2000 | Sogard et al. | |
| 6,142,987 A | 11/2000 | Tsugita | |
| 6,206,868 B1 * | 3/2001 | Parodi | 604/500 |
| 6,245,089 B1 | 6/2001 | Daniel et al. | |
| 6,254,610 B1 | 7/2001 | Darvish et al. | |
| 6,295,989 B1 * | 10/2001 | Connors, III | 128/898 |
| 6,312,444 B1 | 11/2001 | Barbut | |
| 6,315,778 B1 | 11/2001 | Gambale et al. | |
| 6,325,815 B1 | 12/2001 | Kusleika et al. | |
| 6,346,116 B1 | 2/2002 | Brooks et al. | |
| 6,363,900 B1 | 4/2002 | Homi et al. | |
| 6,371,970 B1 | 4/2002 | Khosravi et al. | |
| 6,371,971 B1 | 4/2002 | Tsugita et al. | |
| 6,375,787 B1 | 4/2002 | Lukic | |
| 6,383,205 B1 | 5/2002 | Samson et al. | |
| 6,398,773 B1 | 6/2002 | Bagaoisan et al. | |
| 6,413,235 B1 * | 7/2002 | Parodi | 604/104 |
| 6,537,294 B1 | 3/2003 | Boyle et al. | |
| 6,569,180 B1 * | 5/2003 | Sirhan et al. | 606/194 |
| 6,605,102 B1 | 8/2003 | Mazzocchi et al. | |
| 6,632,236 B2 * | 10/2003 | Hogendijk | 606/198 |
| 6,652,505 B1 | 11/2003 | Tsugita | |
| 6,663,651 B2 | 12/2003 | Krolik et al. | |
| 6,818,006 B2 | 11/2004 | Douk et al. | |
| 6,866,677 B2 | 3/2005 | Douk et al. | |
| 6,887,257 B2 | 5/2005 | Salahieh et al. | |
| 2001/0031982 A1 | 10/2001 | Peterson et al. | |
| 2001/0039411 A1 | 11/2001 | Johansson et al. | |
| 2001/0044598 A1 | 11/2001 | Parodi | |
| 2001/0047184 A1 | 11/2001 | Connors, III | |
| 2001/0049517 A1 | 12/2001 | Zadno-Azizi et al. | |
| 2002/0016564 A1 | 2/2002 | Courtney et al. | |
| 2002/0016565 A1 | 2/2002 | Zadno-Azizi et al. | |
| 2002/0022859 A1 | 2/2002 | Hogendijk | |
| 2002/0026145 A1 * | 2/2002 | Bagaoisan et al. | 604/96.01 |
| 2002/0029031 A1 | 3/2002 | Bagaoisan et al. | |
| 2002/0052638 A1 | 5/2002 | Zadno-Azizi | |
| 2002/0095141 A1 | 7/2002 | Belef et al. | |
| 2002/0121472 A1 | 9/2002 | Garner et al. | |
| 2002/0123765 A1 | 9/2002 | Sepetka et al. | |
| 2002/0143360 A1 | 10/2002 | Douk et al. | |
| 2002/0151927 A1 | 10/2002 | Douk et al. | |
| 2002/0165574 A1 | 11/2002 | Ressemann et al. | |
| 2002/0165598 A1 | 11/2002 | Wahr et al. | |
| 2003/0093106 A1 | 5/2003 | Brady et al. | |
| 2003/0093110 A1 | 5/2003 | Vale | |
| 2003/0125751 A1 | 7/2003 | Griffin et al. | |
| 2003/0212429 A1 | 11/2003 | Keegan et al. | |
| 2004/0049226 A1 | 3/2004 | Keegan et al. | |
| 2004/0082968 A1 | 4/2004 | Krolik et al. | |
| 2004/0220609 A1 | 11/2004 | Douk et al. | |
| 2004/0260277 A1 * | 12/2004 | Maguire | 606/28 |
| 2005/0004553 A1 | 1/2005 | Douk | |
| 2005/0085842 A1 | 4/2005 | Eversull et al. | |
| 2005/0131447 A1 * | 6/2005 | Wahr et al. | 606/194 |
| 2005/0149113 A1 | 7/2005 | Douk et al. | |
| 2006/0004405 A1 | 1/2006 | Salahieh et al. | |

FOREIGN PATENT DOCUMENTS

| | | |
|---|---|---|
| EP | 0 427 429 A3 | 5/1991 |
| EP | 1 181 900 A2 | 2/2002 |
| EP | 1 247 500 A2 | 10/2002 |
| EP | 1 247 500 B1 | 10/2002 |
| EP | 1 351 737 B1 | 10/2003 |
| FR | 267 1282 | 7/1992 |
| WO | WO 92/07606 | 5/1992 |
| WO | WO 96/01591 | 1/1996 |
| WO | WO 99/08744 | 2/1999 |
| WO | WO 99/45835 | 9/1999 |
| WO | WO 00/32266 | 6/2000 |
| WO | WO 00/56391 | 9/2000 |
| WO | WO 00/76390 | 12/2000 |
| WO | WO 01/05462 A1 | 1/2001 |
| WO | WO 01/08743 A1 | 2/2001 |
| WO | WO 01/10343 * | 2/2001 |
| WO | WO 01/10343 A1 | 2/2001 |
| WO | WO 01/15629 A1 | 3/2001 |
| WO | WO 01/21100 A1 | 3/2001 |
| WO | WO 01/70325 A2 | 9/2001 |
| WO | WO 01/70325 A3 | 9/2001 |
| WO | WO 01/70326 | 9/2001 |
| WO | WO 02/11627 A2 | 2/2002 |
| WO | WO 02/062266 A2 | 8/2002 |
| WO | WO 02/087677 A2 | 11/2002 |

OTHER PUBLICATIONS

U.S. Appl. No. 08/748,066, Mazzocchi et al., Nov. 12, 1996 (No. MVA1001USC1).
U.S. Appl. No. 10/051,565, Mazzocchi et al., Jan. 18, 2002 (No. MVA1001USC2).
U.S. Appl. No. 10/051,492, Mazzocchi et al., Jan. 18, 2002 (No. MVA1001USC3).
U.S. Appl. No. 10/051,591, Mazzocchi et al., Jan. 18, 2002 (No. MVA1001USC4).
U.S. Appl. No. 10/051,537, Mazzocchi et al., Jan. 18, 2002 (No. MVA1001USC5).
U.S. Appl. No. 10/051,648, Mazzocchi et al., Jan. 18, 2002 (No. MVA1001USC6).
U.S. Appl. No. 10/060,272, Mazzocchi et al., Jan. 30, 2002 (No. MVA1001USC7).
U.S. Appl. No. 10/060,271, Kusleika et al., Jan. 30, 2002 (No. MVA1002USC1).
U.S. Appl. No. 09/824,910, Kusleika et al., Apr. 3, 2001 (No. MVA1004USC1).
U.S. Appl. No. 10/060,854, Kusleika et al., Jan. 30, 2002 (Ref. No. MVA1004USC2).
U.S. Appl. No. 10/093,572, Kusleika et al., Mar. 8, 2002 (Ref. No. MVA1003US).
U.S. Appl. No. 10/132,562, Anderson et al., Apr. 25, 2002 (Ref. No. MVA1005US).
U.S. Appl. No. 10/194,734, Kusleika et al., Jul. 12, 2002 (Ref. No. MVA1008US).
U.S. Appl. No. 10/096,624, Kusleika et al., Mar. 12, 2002 (Ref. No. F&B file).
US 6,348,062, 02/2002, Hopkins et al. (withdrawn)

* cited by examiner

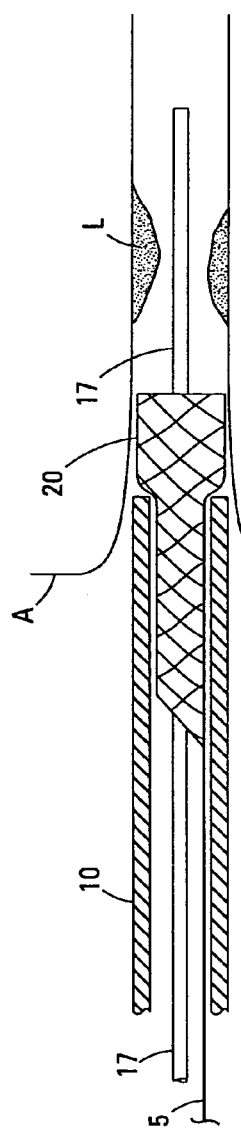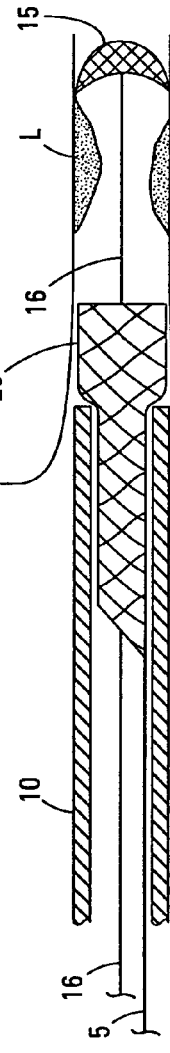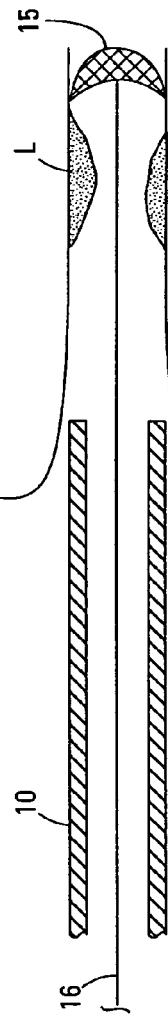

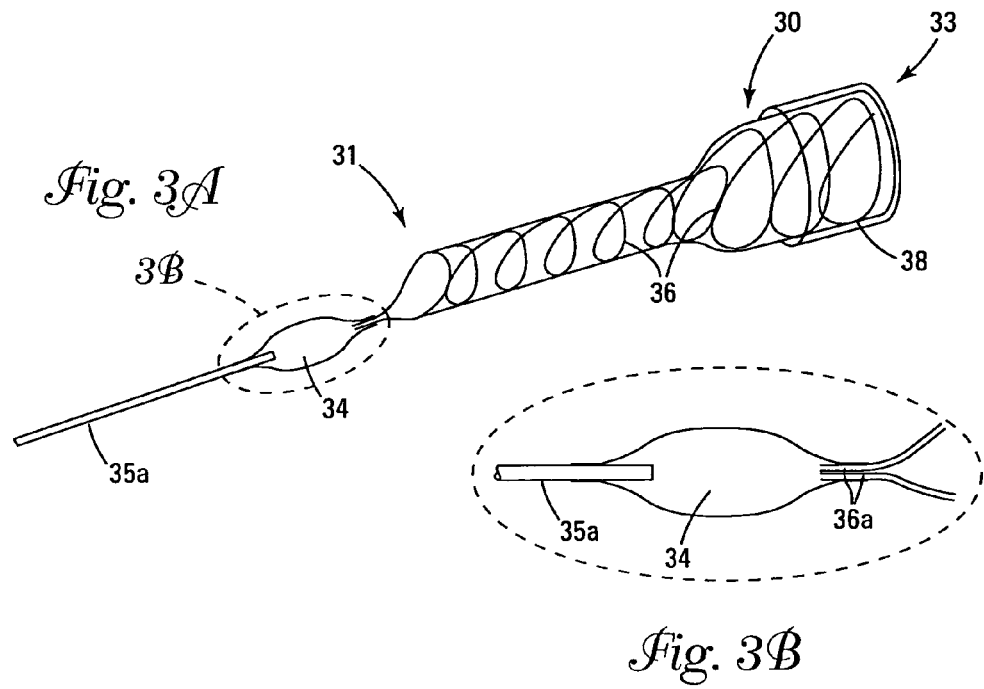
Fig. 3A
Fig. 3B
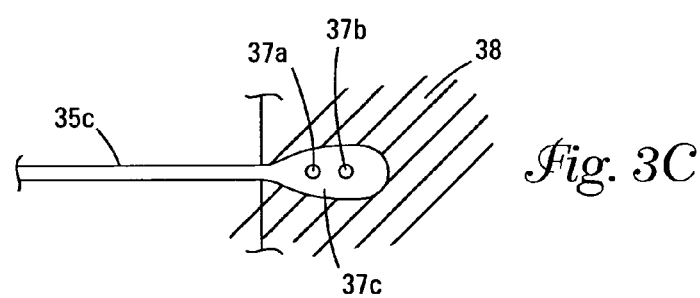
Fig. 3C
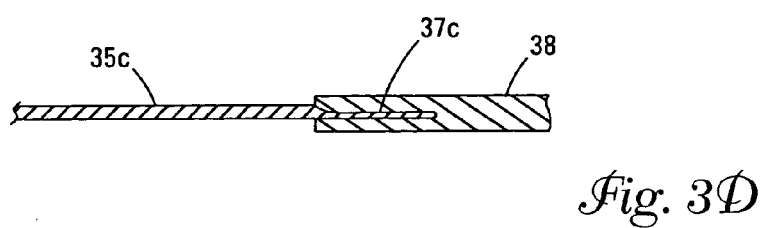
Fig. 3D

DEVICE TO CREATE PROXIMAL STASIS

FIELD OF THE INVENTION

This invention relates to a device, a system, and a method for treating vascular disease. In particular, this invention relates to the occlusion of blood flow through a stenotic region and treatment of the region.

BACKGROUND OF THE INVENTION

Atherosclerosis or vascular disease is the leading cause of death in the world today. It is a disease of the arteries whereby deposits (plaque) build up over time in the walls of the arteries, restricting oxygenated blood flow to vital organs such as the heart, brain and other bodily tissue. A number of medical procedures have been developed to treat vascular disease such as Coronary Artery By-Pass Grafting (CABG) and Percutaneous Balloon Angioplasty (PTCA) and Stenting. These procedures are intended to restore normal flow through the arteries.

In the case of CABG, the saphenous vein is harvested from the leg and used as a conduit to by-pass blood flow from the aorta to a point distal to an obstruction in a coronary artery. After a number of years, these grafts become diseased, and treatment of the graft is needed to improve blood flow. Treatment of these degenerated grafts with PTCA or Stenting is associated with a high incidence of embolic material (vessel deposits) released distally. This can result in a no-flow condition and myocardial infarction. Similarly, treatment of carotid arteries and renal arteries by PTCA and Stenting can cause release of embolic material. In the case of the carotid artery, emboli released can result in a stroke. In the case of the renal artery, emboli release can result in the renal infarct and reduced renal function. There is a risk of embolic material being released with any balloon expansion or passage of a treatment device through a diseased section of a vessel, with undesirable results to the patient. Thus, it is highly desirable to prevent embolic material from being released during treatment of vascular disease.

The use of embolic protection devices has recently improved the outcome for treatment of these diseased grafts and arterial restrictions. There are two major approaches to embolic protection. In either case the devices are delivered to the area of treatment in the conventional means through a guide catheter or elongated sheath.

The first approach involves crossing the obstruction or diseased vessel with a deflated balloon affixed to the distal end of a hollow guidewire. The balloon segment is placed distal to the arterial segment to be treated, and the balloon is inflated to occlude flow of blood in the vessel. The PTCA or Stenting treatment is then performed over the hollow wire and any embolic material is prevented from moving beyond the distal occlusion balloon. After completion of the treatment, a suction catheter is placed into the vessel such that the distal tip is near the balloon. Suction is applied to the catheter tip and embolic material is removed from the vessel.

The second approach involves a filter mounted on a guidewire and sheathed in a delivery catheter. The sheathed filter is placed in the artery distal to the treatment site. The filter is then deployed through the sheath and expands outward adjacent the vessel wall to channel blood flow into the filter. The treatment device is then advanced over the guidewire, and any emboli generated during treatment is directed by the blood flow into the filter. The filter retains embolic material greater in size than the filter pore size. After treatment, a recovery catheter is advanced distally to a location proximal to the filter and the filter pulled proximally. The filter closes and/or the filter is drawn completely into a lumen of the retrieval catheter. The system with captured emboli is then withdrawn from the body.

A balloon occlusion approach can be problematic because no blood is flowing through the vessel during use of the treatment device and ischemia can develop quickly, particularly in saphenous vein grafts. The procedure must be conducted swiftly to prevent undue patient pain. There is also no assurance that all trapped emboli are removed by suction.

A filter approach can be problematic because particles smaller than the filter pore size will pass through the filter and may cause embolic events or consequence, particularly in the brain. There is also no assurance that trapped emboli will not be squeezed through the filter mesh during recovery.

Recent clinical trials show that both types of embolic protection devices reduce the occurrence of embolic events by about half in the case of saphenous vein grafts. Clinical trials currently are assessing the benefit in carotid and other arterial treatments.

Unfortunately, these approaches to embolic protection do not eliminate embolic events entirely because passage of the protection device or the catheter delivering the device across the diseased section of the vessel or lesion can dislodge embolic material prior to deployment of the device. Thus, it would be highly desirable to use a device or method that would prevent release of embolic material during passage of the embolic protection system through the vessel lesion to the deployment location. One prior art attempt to solve this problem is disclosed in U.S. Pat. No. 6,348,062 (Hopkins et al.). In this approach a PTCA balloon is inflated proximal to the treatment site (lesion) to create stasis in the vessel. Emboli liberated on lesion crossing cannot be transported distally because there is no flow. A distal protection filter is then deployed and flow in the vessel is re-established. Any emboli created during lesion crossing by the distal protection device are prevented from flowing distally. The disadvantages of this system are that a treatment balloon must be advanced into the vessel prior to creating stasis, and advancement of this balloon may liberate emboli. Further, initial treatment with a balloon is not appropriate therapy for all procedures. For example, it may be more appropriate to initially debulk a vessel using atherectomy or thrombectomy by methods commonly used in the art. Finally, it is known that even passage of a guidewire can liberate emboli, especially in saphenous vein grafts. Placement of a balloon catheter requires pre-placement of a guidewire in this prior art approach.

SUMMARY OF THE INVENTION

This invention is a device and a method that creates a seal to prevent the flow of blood during the treatment of vascular disease. A seal may be formed between the distal inside diameter of a sheath or catheter such as a guide catheter and within a vessel, such as an artery or vein. An elongated device having a distal portion extending from the catheter and having a fluid impermeable membrane disposed about at least the distal end of the device is used to seal the vessel. This invention is also a system in which the device occludes blood flow and includes a distal protection device which is deployed to filter or remove embolic debris.

In one aspect, this invention is a method of performing an intravascular procedure at a treatment site in a vessel of a patient. The method includes providing a sealing device having proximal and distal ends, a distal sealing portion and a proximal sealing portion and having a lumen extending therethrough. The method further includes introducing a guide catheter into the vessel, advancing the guide catheter through the vessel until a distal end of the guide catheter is at a desired location proximal of the treatment site, introducing the sealing device into a lumen of the guide catheter, advancing the sealing device through the lumen of the guide catheter until the distal sealing portion extends from the distal end of the guide catheter, and occluding the flow of blood through the vessel with the sealing device. After blood flow has been occluded the method includes advancing a distal protection device through the lumens of the guide catheter and the sealing device and through the vessel to a location distal to the treatment site, deploying the distal protection device, withdrawing the distal sealing portion of the sealing device into the guide catheter, advancing a vascular treatment device through the guide catheter to the treatment site, and performing the intravascular procedure with the treatment device.

The distal sealing portion of the sealing device may be expandable from a delivery configuration to a deployed configuration. The proximal sealing portion of the sealing device may have a first diameter and the distal sealing portion may have a second diameter when extended from the distal end of the guide catheter, the second diameter being larger that the first diameter. The sealing device may comprise metal wire, which may comprise nitinol. The sealing device may also have a control element connected adjacent at least one of the distal and proximal ends of the sealing device, and this control element may be a wire or a tube.

The control element may comprise an elongate proximal portion of the sealing device having a length sufficient to extend outside the patient during advancement of the sealing device. The sealing device may comprise a flexible membrane. The distal sealing portion of the sealing element may comprise a flexible membrane which is folded into the lumen of the sealing device, wherein the sealing device further includes a deployment member, and wherein the step of occluding the flow of blood comprises advancing the deployment member through the lumen of the sealing device to push the folded membrane out of the lumen of the sealing device. There may be at least one flow window between the lumen of the sealing device and an exterior surface of the sealing device. When the distal sealing portion is expandable from a delivery configuration to a deployed configuration, there may be a means to delay expansion of the distal sealing portion of the sealing device and this means may include longitudinal restraining elements positioned adjacent the distal sealing portion.

The step of advancing the sealing device may comprise inflating a balloon portion of a balloon catheter in the lumen of the sealing device until the sealing device is secured to the balloon catheter and then advancing the balloon catheter through the lumen of the guide catheter. The sealing device also may include means to bias the proximal sealing portion outwardly to seal against the lumen of the guide catheter, and this biasing means may comprise a spring wire, open cell foam, or a locally thinned portion of the proximal sealing portion. When the treatment site is located adjacent an ostium of the vessel, the distal sealing portion of the sealing device may be provided with a first section with a first diameter sized to seal the vessel proximal to the ostium and a second section with a second larger diameter.

In another aspect, this invention is a method of occluding the flow of blood in a vessel of a patient comprising introducing an elongate sheath into the vessel, the sheath having an inner wall defining a lumen extending therethrough, advancing the sheath through the vessel until a distal end of the sheath is at a desired location in the vessel, introducing a sealing device into the lumen of the sheath, the sealing device having a proximal sealing portion which seals against the inner wall of the sheath and a self-expanding distal sealing portion and having a lumen extending therethrough, and advancing the sealing device through the lumen of the sheath until the distal sealing portion extends from a distal end of the sheath and expands to seal against the wall of the vessel to occlude blood flow.

In another aspect, this invention is a sealing device for use in combination with a catheter to occlude fluid flow through a body lumen comprising an elongate body having a distal sealing portion and a proximal sealing portion and a lumen extending therethrough, the proximal sealing portion being sized to seal against a lumen of the catheter and the distal sealing portion being sized to seal against the body lumen when the distal sealing portion is extended from a distal end of the catheter.

In another aspect, this invention is a system for occluding the flow of blood in a vessel of a human vascular system comprising a catheter having proximal and distal ends and a lumen, and a sealing device having a proximal sealing portion and a distal sealing portion and a lumen, the proximal sealing portion being sized to seal against the lumen of the catheter and the distal sealing portion being sized to seal against the wall of the vessel when the distal sealing portion is extended from the distal end of the catheter.

In another aspect, this invention is a system for protecting a patient from emboli released during an intravascular procedure performed at a treatment site in a vessel of a patient comprising a guide catheter having proximal and distal ends and a lumen, a sealing device having a distal sealing portion and a proximal sealing portion and a lumen, the proximal sealing portion being sized to seal against the lumen of the guide catheter and the distal sealing portion being sized to seal against the wall of the vessel at a location proximal to the treatment site when the distal sealing portion is extended from the distal end of the guide catheter, and a distal protection device sized to be delivered through the lumens of the guide catheter and sealing device to a location in the vessel distal to the treatment site.

In another aspect, this invention is a system for protecting a patient from emboli released during an intravascular procedure performed at a treatment site in a vessel of a patient comprising a guide catheter having proximal and distal ends and a lumen, a sealing device having a lumen and having a proximal portion including proximal sealing means for sealing against the lumen of the guide catheter and a distal portion including distal sealing means for sealing against the wall of the vessel at a location proximal to the treatment site when the distal portion is extended from the distal end of the guide catheter and a distal protection device sized to be delivered through the lumens of the guide catheter and sealing device to a location in the vessel distal to the treatment site. The proximal sealing means may comprise a spring wire or open cell foam. A distance between a wall of the lumen of the sealing device and an exterior surface of a first section of the proximal portion defines a first wall thickness and a distance between the wall of the lumen of the sealing device and an exterior surface of a second section of the proximal portion defines a second wall thickness which is less than the first wall thickness, the second section being biased radially outwardly, the proximal sealing means comprising the second section. The distal sealing means may comprise a self-expanding metal.

In another aspect, this invention is a system for protecting a patient from emboli released during an intravascular procedure performed at a treatment site in a vessel of a patient comprising a guide catheter having proximal and distal ends and a lumen, a sealing device having a distal sealing portion and a proximal sealing portion and a lumen, the proximal sealing portion being sized to seal against the lumen of the guide catheter and the distal sealing portion being sized to seal against the wall of the vessel at a location proximal to the treatment site when the distal sealing portion is extended from the distal end of the guide catheter, a delivery catheter having distal and proximal ends and a lumen, the delivery catheter being sized to be delivered through the lumens of the guide catheter and sealing device to a location in the vessel where its distal end is distal to the treatment site, and an elongate support member carrying an embolic protection device, the elongate support member and embolic protection device being sized to be slideably accommodated within the lumen of the delivery catheter, the embolic protection device being expandable from a delivery configuration when contained within the delivery catheter to a deployed configuration when extended from the distal end of the delivery catheter.

In another aspect, this invention is a method of performing an intravascular procedure at a treatment site in a vessel of a patient comprising providing a sealing device having proximal and distal ends, a distal sealing portion and a proximal sealing portion and having a lumen extending therethrough, introducing a guide catheter into the vessel, the guide catheter having proximal and distal ends and a lumen and a valve connected at the proximal end for opening and closing the lumen of the guide catheter to fluid flow, advancing the guide catheter through the vessel until the distal end of the guide catheter is at a desired location proximal of the treatment site, introducing the sealing device into the lumen of the guide catheter, advancing the sealing device through the lumen of the guide catheter until the distal sealing portion extends from the distal end of the guide catheter, blocking antegrade blood flow through the vessel with the sealing device, opening the valve on the guide catheter to create retrograde blood flow through the vessel, after antegrade blood flow has been blocked advancing a distal protection device through the lumens of the guide catheter and the sealing device and through the vessel to a location distal to the treatment site, deploying the distal protection device, withdrawing the distal sealing portion of the sealing device into the guide catheter, advancing a vascular treatment device through the guide catheter to the treatment site, and performing the intravascular procedure with the treatment device.

In another aspect, this invention is a method of performing an intravascular procedure at a treatment site in a vessel of a patient comprising providing a sealing device having proximal and distal ends, a distal sealing portion and a proximal sealing portion and having a lumen extending therethrough, introducing a guide catheter into the vessel, the guide catheter having proximal and distal ends and a lumen and a suction device connected to the lumen, advancing the guide catheter through the vessel until the distal end of the guide catheter is at a desired location proximal of the treatment site, introducing the sealing device into the lumen of the guide catheter, advancing the sealing device through the lumen of the guide catheter until the distal sealing portion extends from the distal end of the guide catheter, blocking antegrade blood flow through the vessel with the sealing device, operating the suction device to create retrograde blood flow through the vessel, after antegrade blood flow has been blocked advancing a distal protection device through the lumens of the guide catheter and the sealing device and through the vessel to a location distal to the treatment site, deploying the distal protection device, withdrawing the distal sealing portion of the sealing device into the guide catheter, advancing a vascular treatment device through the guide catheter to the treatment site, and performing the intravascular procedure with the treatment device.

In another aspect, this invention is a system for creating retrograde flow of blood in a vessel of a human vascular system comprising a catheter having proximal and distal ends and a lumen and a valve connected at the proximal end for opening and closing the lumen of the catheter to fluid flow, and a sealing device having a proximal sealing portion and a distal sealing portion and a lumen, the proximal sealing portion being sized to seal against the lumen of the catheter and the distal sealing portion being sized to seal against the wall of the vessel when the distal sealing portion is extended from the distal end of the catheter.

In another aspect, this invention is a system for creating retrograde flow of blood in a vessel of a human vascular system comprising a catheter having proximal and distal ends and a lumen, a suction device connected to the lumen of the catheter, and a sealing device having a proximal sealing portion and a distal sealing portion and a lumen, the proximal sealing portion being sized to seal against the lumen of the catheter and the distal sealing portion being sized to seal against the wall of the vessel when the distal sealing portion is extended from the distal end of the catheter.

In another aspect, this invention is a method of delivering an embolic protection device to a desired location distal to a treatment site in a vessel of a patient. The method includes providing a sealing device having proximal and distal ends, a distal sealing portion and a proximal sealing portion and having a lumen extending therethrough, introducing a guide catheter into the vessel, advancing the guide catheter through the vessel until a distal end of the guide catheter is at a desired location proximal of the treatment site, introducing the sealing device into a lumen of the guide catheter, advancing the sealing device through the lumen of the guide catheter until the distal sealing portion extends from the distal end of the guide catheter, occluding the flow of blood through the vessel with the sealing device, and after blood flow has been occluded advancing a distal protection device through the lumens of the guide catheter and the sealing device and through the vessel to the desired location distal to the treatment site.

In another aspect, this invention is a method of occluding the flow of blood in a vessel of a patient comprising providing a sealing device having proximal and distal ends, a distal sealing portion and a proximal sealing portion and having a lumen extending therethrough, introducing a guide catheter into the vessel, advancing the guide catheter through the vessel until a distal end of the guide catheter is at a desired location proximal of the treatment site, introducing the sealing device into a lumen of the guide catheter, and advancing the sealing device through the lumen of the guide catheter until the distal sealing portion extends from the distal end of the guide catheter and expands to seal against a wall of the vessel.

BRIEF DESCRIPTION OF THE DRAWINGS

FIGS. 2A to 2F are detailed illustrative views of the system of this invention, showing deployment of the guide seal and a distal protection device within a vessel.

FIG. 3A is a perspective view of a device of this invention attached to a proximal control wire. FIG. 3B is a detail view showing a crimp tube that attaches the control wire and the proximal end of the guide seal; FIG. 3C is a top view of an alternate attachment means, and FIG. 3D is a cross sectional view showing the attachment means of FIG. 3C.

DETAILED DESCRIPTION OF THE PREFERRED EMBODIMENTS

Figure 1A:
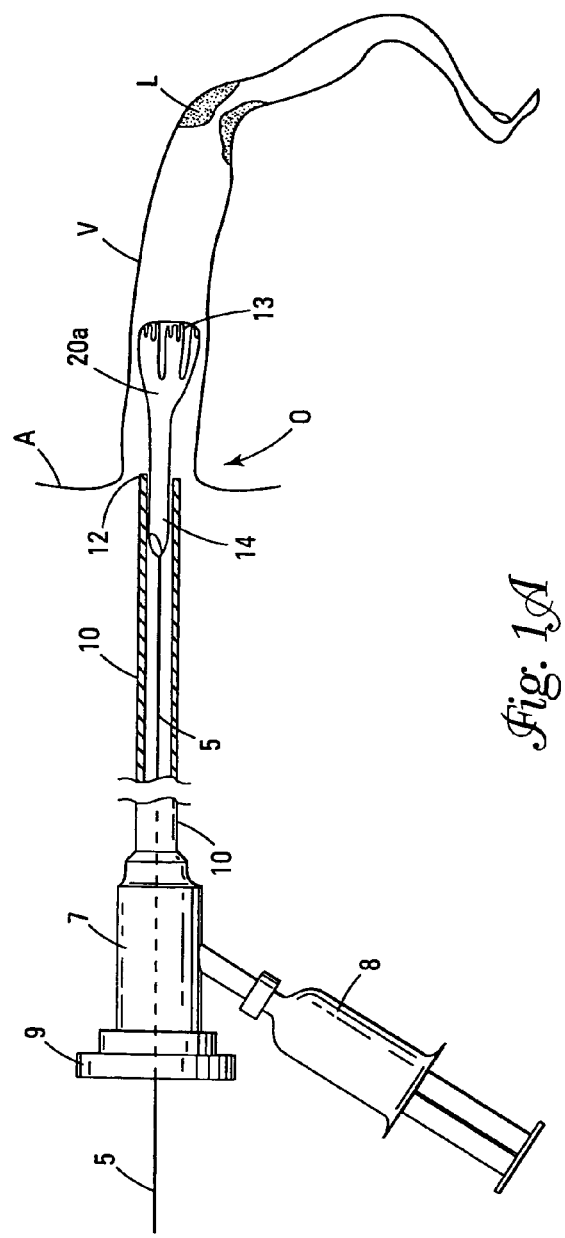
FIG. 1A is a side view in partial cross-section of one embodiment of the device of this invention and the delivery system used to deliver it.

The terms "distal" and "proximal" as used herein refer to the relative position of the guidewire, catheters, and guide seal in a lumen. "Proximal" refers to a location upstream and "distal" refers to a location downstream. Flow of blood through a lumen normally moves from the proximal to the distal portions of the device of this invention, however, the device interrupts this flow and a retrograde flow may be established.

The Figures describe various embodiments. Elements that vary from one embodiment to another but otherwise are similar in shape, size, relative placement, or function are denoted by suffices "a", "b", "c", etc., and may be referred to in a general way by a number without its suffix.

The present invention is a device for occluding blood flow in a vessel at a location proximal to a treatment site in the vessel, thus preventing embolic material from moving distally in the vessel, prior to deployment of an embolic protection device positioned distally of the treatment site. The device includes a guide seal that has a proximal portion that seals within the lumen of a guide catheter and a distal portion that expands when deployed beyond the distal end of the guide catheter to seal within a vessel so that a fluid tight seal is obtained. The guide seal stops blood flow through the vessel and is deployed without causing damage to the vasculature. A filtration device or other distal protection device can then be advanced through the guide seal, down the vessel, and across a lesion or stenosis. Because of the occlusion by the guide seal there is little or no flow through the stenotic site when it is being crossed by the distal protection device or its delivery catheter. A proximal wire or other control means extends axially and controls actuation of the guide seal by its position relative to the distal end of the guide catheter.

The guide catheter, guide seal, control wires and other components of the device of this invention comprise biocompatible materials, and these include metals and polymeric materials. These materials can be treated to impart biocompatibility by various surface treatments, as known in the art. Desired components also may be coated with anti-thrombogenic materials such as heparin or materials to enhance slipperiness such as hydrophilic coatings.

Wire is selected on the basis of the characteristic desired, i.e., stiffness or flexibility, and the properties can depend upon both the diameter of the wire and its cross-sectional shape. The size, thickness and composition of elastic materials are selected for their ability to perform as desired as well as their biocompatibility. It is to be understood that these design elements are all within the scope of this invention.

The guide seal comprises an elongate body defining an interior cavity which, when deployed in a vessel, is large enough to allow passage of a catheter used to deliver a distal protection device such as an expandable filter or balloon. It has a sealing membrane around at least the portion of the guide seal which extends distally of the guide catheter when the guide seal is deployed. In a preferred embodiment, the guide seal has a vessel sealing portion adjacent its distal end and a guide catheter sealing portion which remains in the lumen of the guide catheter when the guide seal is deployed. The guide catheter sealing portion lies within the guide catheter and can expand to seal within the guide catheter. Typically, the vessel sealing portion ranges in diameter from about 2 to about 10 mm and has a larger diameter than the guide sealing portion, which ranges in diameter from about 1.27 mm to about 2.8 mm (0.050 inch to 0.110 inch). The guide seal is open at its distal end to provide for the passage of another catheter or a distal protection element, as described further below.

The guide seal may comprise any material that is suitably flexible and resilient and may comprise braided, knitted, woven, or non-woven fabrics, or polymer films, such as polyester, nylon, and the like. The guide seal may comprise stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, and the like. A preferred shape memory metal comprises nickel and titanium and is known as "nitinol". This is commercially available in various dimensions.

In a preferred embodiment, the guide seal is formed by braiding 16 nitinol wires measuring about 0.001 inch by 0.003 inch (0.025 mm by 0.076 mm) with a pick count of about 50 to 100. Alternatively, round wires having a diameter of about 0.0015 inch (0.038 mm) diameter, (range of 0.0007 inch to 0.002 inch, or 0.018 mm to 0.054 mm) with various pick counts, can be used as needed to achieve adequate combination of flexibility and support of a covering or attached membrane for fluid sealing. Braiding options are well known in the catheter industry and also described in co-pending, commonly assigned U.S. Ser. No. 08/748,066 (Mazzochi et al.), hereby incorporated herein by reference. The guide seal is preferably about 6 inches (15.4 cm) long with a range from about 2 to 20 inches (about 5.1 to 50.8 cm).

A sealing membrane may be cast onto the wire of the elongate body of the guide seal by using an elastomer that allows free diameter expansion from a smaller constrained diameter. A cast membrane may be made using a two part silicone dispersion such as that commercially available as Med-6640 from Nusil Technology, Carpinteria, Calif. Use of dipping technology is well known in the industry. Alternatively, a thin membrane may be attached to or carried by the braid by means of adhesives, sutures, thermowelding or other techniques know by those of skill in the art for covered stents and vascular grafts. U.S. Pat. Nos. 6,139,573 (Sogard et al.) and 5,824,044 (Quiachon et al.) teach the use of polymer and ePTFE membranes attached to either side of an expandable metal stent. U.S. Pat. No. 6,375,787 (Schneider) teaches attachment of elastic tubular sleeves on expandable wire braided stents. Numerous polymer materials may be used such as PTFE, urethanes, silicones, polyethylene, and elastomeric materials to form a fluid impermeable layer or membrane. Suitable elastomeric materials include polyamide block copolymers (commercially available under the trade designation "PEBAX").

In a preferred embodiment where nitinol braided wire is used, the proximal and distal diameters of the elongate body of the guide seal may be heat set to limit the expansion force against the guide catheter and against the vessel. Adequate force is needed to produce a good seal, but too much expansion force can cause drag, making it difficult to move the guide seal through the lumen guide catheter. Such heat set parameters are described in patent application WO 96/01591 (Mazzochi et al.) and well known in the art. The proximal portion of the expandable member that seals to the guide catheter would be provided with an outside diameter in the range of 4 to 14 French in the self expanded state depending on the guide catheter diameter and the sealing pressure needed. A typical guide catheter or sheath is 6 to 10 French outside diameter, with 6 to 8 French being most common. In the case of an 8 French guide catheter, the proximal section of the guide seal may have a diameter of 6 French, for example. The distal portion of the guide seal (i.e., that which will seal against the inside of the vessel) would have an expanded diameter 10 to 20% bigger than the vessel diameter. For example, typical saphenous vein grafts have an inside diameter ranging from 3 to 5 mm and carotid arteries have inside diameters ranging from 5 to 7 mm.

Suitable materials for the proximal control wire include stainless steel, nitinol, alloys such as cobalt-chromium-nickel-molybdenum-iron alloy (commercially available under the trade designation Elgiloy™) or other resilient material. In a preferred embodiment, the proximal wire is a stainless steel wire in the range of 0.010 to 0.018 inch (0.025 cm to 0.046 cm) diameter, preferably 0.014 inch (0.036 cm) and preferably about 170 cm long. This wire preferably is coated with polytetrafluoroethylene (PTFE) for lubricity.

A distal protection element may be used in conjunction with the guide catheter and guide seal of this invention. A distal protection element includes any device to be deployed in a lumen or vessel of a patient in a minimally invasive procedure. Suitable distal protection elements include occlusive devices and filtration devices. Occlusive devices include balloons, i.e., elements that are designed to expand within a vessel. Filters include, for example, those disclosed in commonly assigned, co-pending U.S. Ser. No. 10/602,271, entitled "Slideable Vascular Filter", U.S. Ser. No. 10/093,572, entitled "Distal Protection Devices Having Controllable Wire Motion", and U.S. Ser. No. 10/132,562, entitled "Vascular Protection Devices and Methods of Use", hereby incorporated herein by reference.

The distal protection element used in conjunction with the guide seal and guide catheter may comprise a self-expanding material. These include metals such as stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, silk, and the like. A shape memory metal is particularly suitable for those applications when it is desired for an element, such as a filter, to assume a pre-determined three-dimensional shape or for a guidewire to maintain a pre-determined curvature. A preferred shape memory metal is nitinol. For example, nitinol tubular braid can be heat set into a desired shape, compressed for delivery to a site, and then released to form the heat-set shape.

One or more radiopaque markers may be positioned at various locations on the guide seal, the guide catheter, or the distal protection element. These radiopaque markers or marker bands comprise a material that will strongly absorb X-rays and thus assist in proper placement. Suitable radiopaque materials include platinum, gold, iridium, tungsten, bismuth subcarbonate, barium sulfate, and others known to one of skill in the art.

The various embodiments of the invention will now be described in connection with the figures. It should be understood that for purposes of better describing the invention the drawings have not been made to scale. Further, some of the figures include enlarged or distorted portions for the purpose of showing features that would not otherwise be apparent. The material comprising the guide seal is indicated by cross-hatching in some of the figures but is omitted from others for simplicity and to show particular features of the device.

As is known in the art, in treatment of a blood vessel, such as a saphenous vein by-pass graft, a physician first places an introducer catheter into the femoral artery. This introducer catheter is used to position a guide catheter and guidewire so that other catheters can be moved along the guidewire to a treatment site. For simplicity, the guidewire, guide catheter, and introducer catheter are not shown.

Figure 1B:
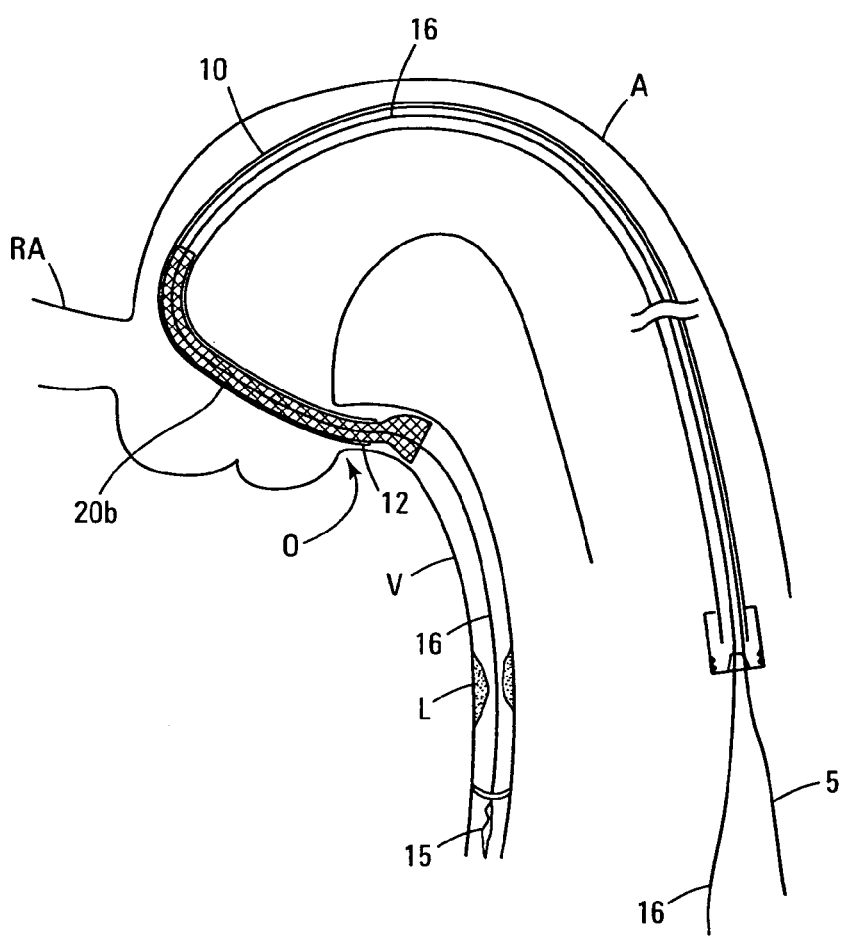
FIG. 1B is a detail view showing deployment of another embodiment of the device of this invention within a saphenous vein graft.

The use of the device of this invention can be understood with reference to FIGS. 1A and 1B. FIG. 1A shows a simplified linear view of the arrangement of a guide catheter 10 used in connection with the novel guide seal 20a of the present invention. A Y connector 7 is attached to the proximal end of the guide catheter. The distal end 12 of the guide catheter is shown inserted in the ostium O of a coronary vessel V which has a lesion L. The coronary vessel may be a saphenous vein graft from a previous bypass surgery. Guide seal 20a is shown with a distal vessel sealing portion 13 deployed beyond the distal end of the guide catheter expanded against the walls of the vessel and a proximal guide catheter sealing portion 14 which seals against the lumen of the guide catheter. FIG. 1B shows guide catheter 10 that has been advanced through the aortic arch past the right coronary artery RA so that its distal end is within the ostium of the vessel. Guide seal 20b has been deployed to occlude the vessel and a distal protection device 15 mounted on an elongate support member 16 has been advanced across the lesion. The guide seal may be coated inside and out with a slippery coating to facilitate its passage through the guide catheter and to facilitate passage of devices through the guide seal.

A Y connector with hemostasis valve typically is attached to the proximal end of the guide catheter for ease of device passage and reduced blood loss. In a preferred embodiment, control wire 5, which is connected to the proximal end of the guide seal, passes through the Y connector 7. Hemostasis valve 9 is at the proximal end of Y connector 7. Optional locking syringe 8 is connected to a side arm of the Y connector. The purpose of the locking syringe is to create suction and flow reversal if desired during the time the vessel is sealed. The locking syringe operates by withdrawal of a plunger until the plunger locks into position, thus creating suction in the syringe. This is done while tightening hemostasis valve 9 to prevent entry of air into the guide.

The use of the device is as follows. The physician first places an introducer catheter into the femoral artery. A guidewire is then advanced through the femoral artery into the aorta. The guide catheter is then advanced over the guidewire until the distal tip of the guide catheter is in the ostium of the vessel. The guidewire is then removed. The guide seal is then loaded into the proximal end of the guide catheter through the Y connector with the aid of an introducer and advanced distally by moving control wire 5 in a distal direction. The guide seal is advanced until its distal tip is just proximal of the distal tip of the guide catheter. Then, the embolic protection device of choice which is typically carried on an elongate support member such as a guidewire and delivered within a delivery catheter is advanced through the guide catheter along side control wire 5 until its distal end is just proximal of the distal end of the guide catheter. At this position the embolic protection device is within the lumen of the guide seal. The guide seal is then advanced distally until sufficient length is extended to ensure full diameter contact of the distal sealing portion with the inside diameter of the vessel wall. When the guide seal is used in the ostium of a coronary artery it may be provided with structural features which prevent the distal sealing portion from expanding too rapidly which could result in the distal tip of the guide catheter being dislodged from the ostium. These features are discussed in detail hereafter. Deployment of the distal sealing portion of the guide seal results in a seal being formed between the guide catheter and the vessel which occludes the flow of blood through the vessel. The proximal end of the guide catheter may be closed to stop flow in the vessel or may be opened to atmosphere to achieve retrograde flow from the vessel proximally through the guide catheter during vessel sealing. Alternatively, the hemostasis valve on the Y connector may be closed and the syringe plunger on the Y connector sidearm locked in a withdrawn position to cause vacuum in the syringe barrel and resultant flow reversal in the vessel and proximally through the guide. The embolic protection device is now advanced through the guide seal and through the vessel across the lesion to a point distal to the treatment site. Any embolic material dislodged by passage or deployment of the embolic protection device is prevented from flowing distally due to no flow or reverse flow in the vessel. In the case of retrograde flow embolic material can be flushed proximally through the guide catheter. Once the embolic protection device is deployed and its delivery catheter (if used) is removed, the guide seal is retracted proximally into the guide catheter and optionally removed from the patient in either an over-the-wire or rapid exchange manner. At this time if the embolic protection device is a filter, flow is re-established in the vessel and any embolic material in the vessel is carried by the flow into the filter where it is captured for later removal. If the embolic protection device is an occlusive device such as a balloon the embolic material is prevented from escaping the vessel until a suction catheter is deployed for its removal or the guide catheter may be used for extraction by connecting a suction source to its proximal end or to the side arm of the Y connector.

Figure 1C:
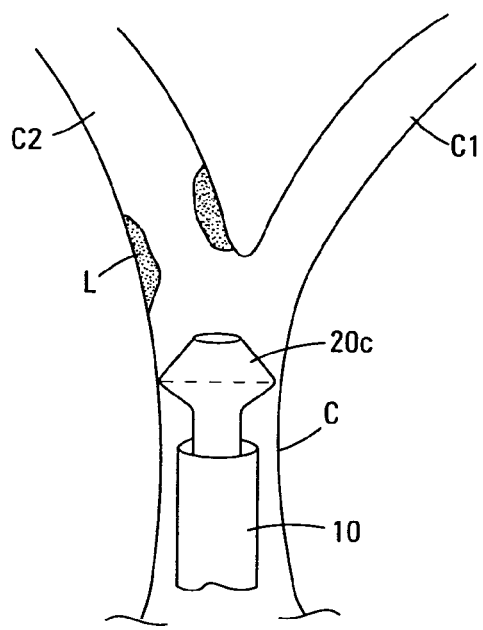
FIG. 1C is an illustrative view of deployment of another embodiment of the device of this invention in a carotid artery.

It is to be understood that the device of this invention could be used in any desired vessel, such as, for example, the right main coronary artery, the bracheocephalic artery, or renal arteries. FIG. 1C illustrates the use of the device of this invention in carotid artery C. The distal sealing portion of a guide seal 20c is shown deployed beyond the distal end of catheter 10. The guide seal is proximal to external carotid artery C1 and internal carotid artery C2. Lesion L is present in the internal carotid artery. The guide seal is able to seal the common carotid artery and then the lesion can be treated as described above. Satisfactory guide sealing occurs when the guide seal is in its expanded form and its distal end is out of the distal end of the catheter. Since the distal end of the guide catheter is not engaged with a vessel ostium it is not necessary for the guide seal to be provided with delayed expansion properties as discussed hereafter.

Figure 1D:
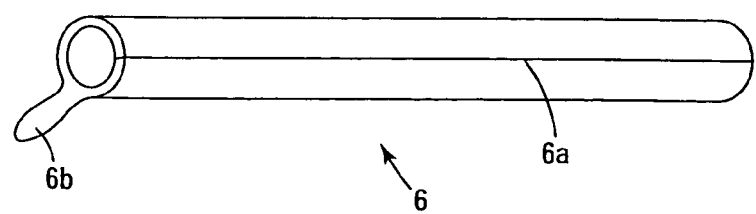
FIG. 1D is a perspective view of an introducer used to load the guide seal into the system.

FIG. 1D illustrates introducer 6, which is used to load guide seal 20 (attached to proximal control wire 5) into Y connector 7. Introducer 6 is a cylinder having longitudinal slit 6a and tab 6b. Guide seal 20 is back-loaded into introducer 6. Introducer 6 is then positioned in the Y connector until it abuts the proximal end of the guide catheter. Then the guide seal is pushed into the guide catheter and the introducer is withdrawn from the Y connector. The introducer is then pulled sideways off the control wire (i.e., the control wire passes through the slit). Tab 6b facilitates gripping the introducer, pulling it out of the Y connector, and pulling it off the control wire. Optionally, the guide seal could be pre-loaded into the guide catheter before the guide is advanced into the aorta. Optionally the introducer could be provided with a larger proximal diameter, tapered to meet the distal diameter, to facilitate front loading the catheter with the sealing cuff into the introducer.

Figure 2A:
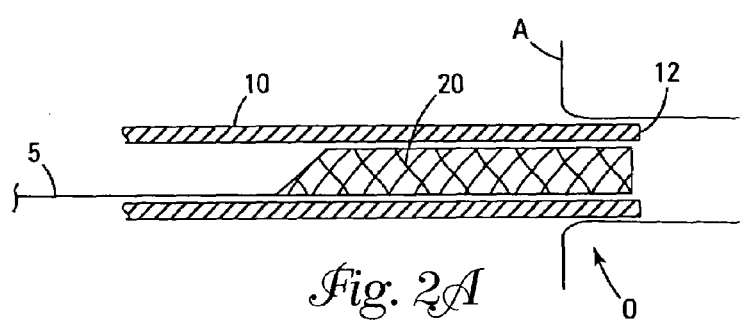

FIGS. 2A to 2F illustrate in a simplified manner the stepwise deployment of the guide seal in a coronary artery. FIG. 2A shows guide seal 20 attached to proximal control wire 5 inside guide catheter 10. The distal end 12 of guide catheter 10 is in position at the desired ostium O and guide seal 20 has been advanced through the guide catheter to a desired position adjacent the distal end of the guide catheter.

Figure 2B:
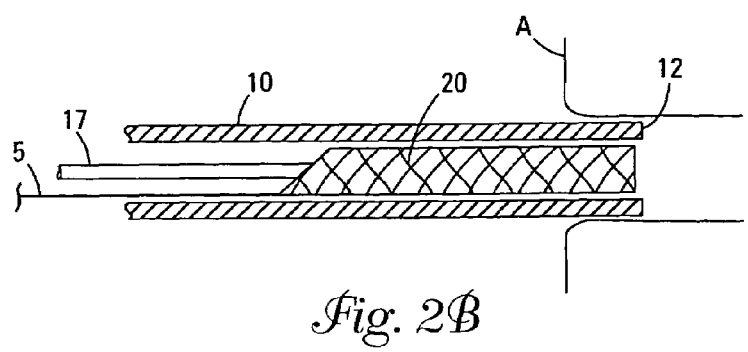
Figure 2C:
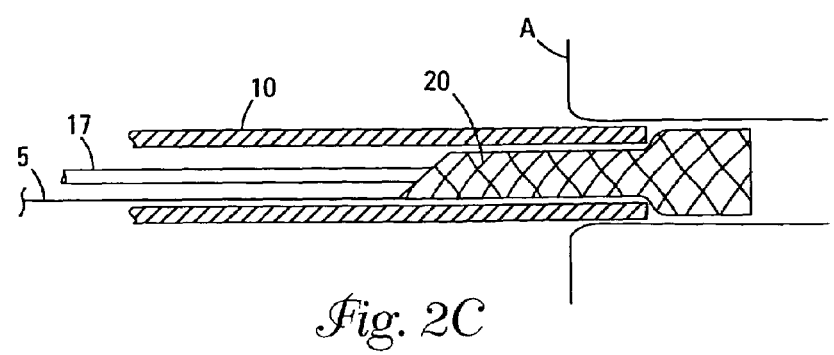

FIG. 2B shows the delivery catheter 17 of the embolic protection device advanced to a position where its distal end is adjacent the distal end of the guide catheter and within the lumen of the guide seal. FIG. 2C shows the guide seal having been advanced distally so that its distal sealing portion seals against the walls of the vessel. At this point flow through the vessel has been stopped. After flow has stopped, a distal protection device is advanced through guide seal 20 into the lumen of the vessel and across lesion L as shown in FIG. 2D. FIG. 2E shows delivery catheter 17 having been withdrawn proximally resulting in the deployment of a distal protection device 15 distal to the region of the lesion. In FIG. 2F the guide seal has been withdrawn proximally out of the guide catheter, flow has been re-established, and debris from the lesion collected by filter 15. At this point a treatment device of choice (i.e., a balloon, atherectomy device, stent) or a combination thereof may be advanced over elongate support member 16 to the treatment site. When the procedure is finished, the embolic protection device is withdrawn into a recovery catheter or into the guide catheter and both are removed from the patient.

Various alternative embodiments of guide seals and particular features thereof are described in connection with FIGS. 3 to 16.

FIG. 3A illustrates guide seal 30 having proximal end 31 and distal end 33. The guide seal is substantially tubular and comprises stainless steel or nitinol braid 36 attached at its proximal end 31 to control wire 35a by crimp tube 34. Guide seal 30 is covered over at least a portion adjacent the distal end 33 (i.e., in the sealing area) with a fluid impermeable membrane 38 such as silicone, urethane, polyethylene, polytetrafluoroethylene (PTFE), and the like. Proximal end 31 has a first diameter, and distal end 33 has a larger second diameter that expands to seal against the wall of the vessel. Proximal end 31 is preferably cut or formed at an angle to the seal axis to facilitate unimpeded entry of the seal's proximal end into the distal end of the guide catheter.

FIGS. 3B to 3D are detail views that show how the distal end of the control wire 35a can be attached to the proximal end of the guide seal. In FIG. 3B, wires 36a making up braid 36 are gathered together and inserted in one end of crimp tube 34. Wires 36a are gathered at the proximal end of the guide seal before membrane 38 is applied to braid 36. The gathered wires are inserted in the distal end of the crimp tube and the tube is crimped on to the wire. Proximal control wire 35 is inserted into the proximal end of the crimp tube and the tube similarly crimped to the wire. Adhesives may be used in addition to or in place of crimping. Tube 34 is preferable a stainless steel hypotube and may be tapered at one or both of the proximal and distal ends.

FIGS. 3C and 3D illustrate a top view and a sectional side view of an alternative connection arrangement of the guide seal and control wire. End 37c of control wire 35c is flattened and provided with one or more holes (two are shown here) 37a and 37b that facilitate the attachment of the end of the wire to impermeable polymer membrane 38. For simplicity of illustration, braid 36 is not shown in these two figures. In this embodiment end 37c is embedded in the impermeable membrane.

Figure 4A:
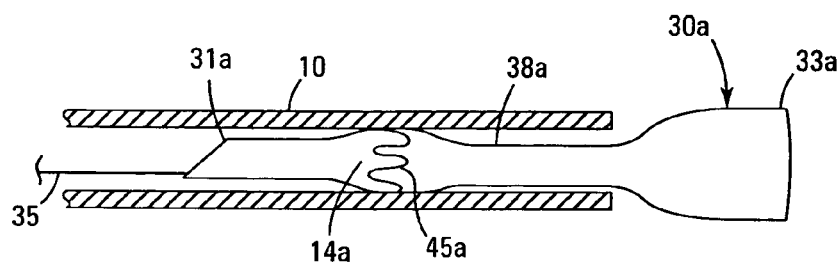
FIGS. 4A to 4C are side views of alternate embodiments of the device of this invention showing means for sealing the guide seal within the lumen of the guide catheter.
Figure 4B:
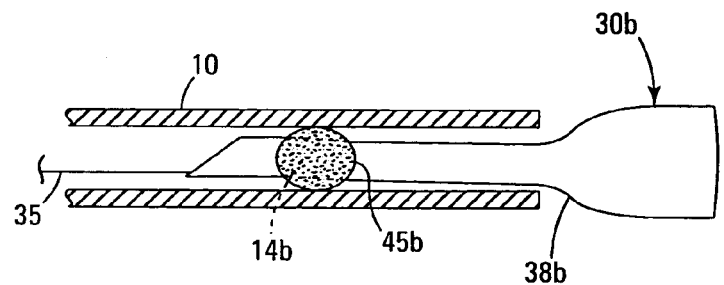
Figure 4C:
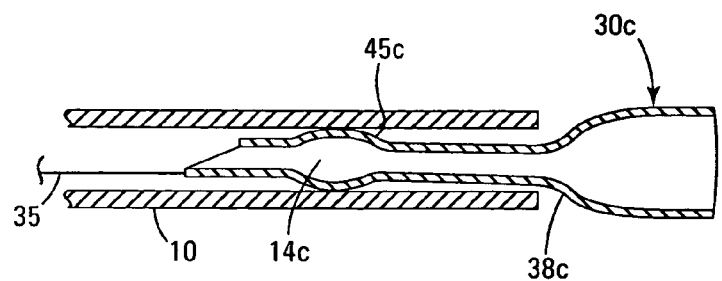

The guide seal may be constructed with special features which enhance the effectiveness of the seal between the proximal or guide catheter sealing portion and the inner wall of the guide catheter. FIGS. 4A to 4C are detail views illustrating various ways to incorporate a range of guide seal diameters so that a seal within the guide catheter can be obtained. Guide catheter 10 is shown in cross section. In FIG. 4A, guide seal 30a is attached to control wire 35 and has proximal end 31a and distal end 33a. Spring wire 45a is embedded within polymeric membrane 38a in guide seal portion 14a and operates to seal the region between the guide seal and the guide catheter. In FIG. 4B, guide seal 30b has an open cell foam 45b mounted on the impermeable polymeric membrane 38b in guide seal portion 14b, thus forming a seal. Suitable foams include those comprising polyurethane, polyvinylalcohol, and the like. In FIG. 4C, guide seal 30c comprises polymeric membrane 38c that has a locally thinned expanded diameter area 45c in guide seal portion 14c. This thinned area functions to seal guide catheter 10. For example, the wall thickness of the guide seal may be about 0.005 inch (0.13 mm) except at the locally thinned portion where it is about 0.001 inch (0.025 mm).

Figure 5A:
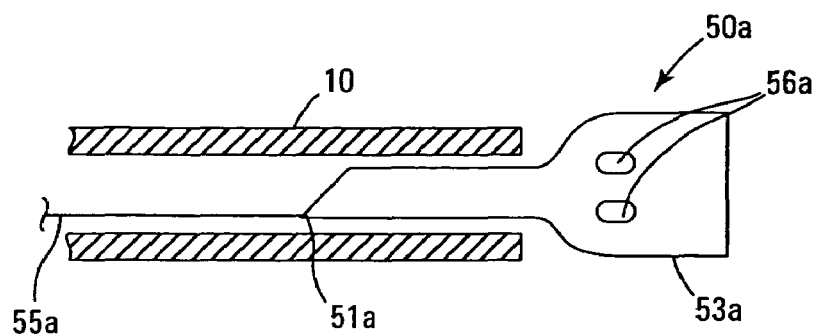
FIGS. 5A and 5B are side views of the device of this invention provided with flow windows.
Figure 5B:
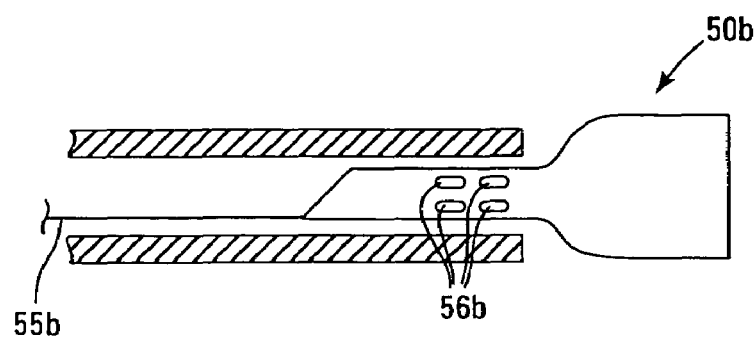

In some instances, a patient may not be able to tolerate static or reversed blood flow for any length of time. In this case, it is possible to provide an option to rapidly establish blood flow in the vessel during use of the guide seal. FIGS. 5A and 5B illustrate guide seals 50a and 50b in which one or more flow windows (56a or 56b) are provided. FIG. 5A shows guide seal 50a attached to proximal control wire 55a at proximal end 51a with two flow windows 56a positioned toward distal end 53a, i.e., at the expanded distal region of the seal. Similarly, FIG. 5B shows guide seal 50b having four flow windows 56b at the unexpanded region of the seal near the distal end of guide catheter 10. In use, the flow windows are normally positioned within the guide catheter when the vessel sealing portion is deployed distally to seal the vessel and establish stasis. In those cases where the patient cannot tolerate the stasis or retrograde flow situation the guide seal is further advanced distally out of the guide catheter to expose the flow windows. This allows some flow through the flow windows to relieve the patient's symptoms. This design allows relief to be provided to the patient without removing the guide seal from engagement with the vessel wall. Alternatively, the guide seal may be positioned to normally allow flow through the flow windows. The guide seal is then withdrawn into the guide catheter to cover the flow windows only during steps likely to create emboli such as lesion crossing and lesion dilatation. Radiopaque materials may be added to the guide seal if it is desired to visualize the location of the flow windows.

If the system disclosed herein is used in the ostium of an artery, such as a coronary artery, it is desirable to maintain the position of the distal end of the guide catheter within the ostium during the course of the procedure in order to provide access to the artery for various interventional devices. During deployment of the distal vessel sealing portion of the guide seal by advancing the guide seal distally it is possible to dislodge the distal end of the guide catheter from the ostium if the distal end of the guide seal self-expands too quickly. This is because the distal end of the guide seal will engage the vessel wall before the entire vessel sealing portion has been advanced distally out of the guide catheter. Further advancement of the guide seal after the vessel wall is engaged can result in dislodging the distal end of the guide catheter from the ostium. Thus, it is preferred to have a means to control the expansion of the distal end of the guide seal.

Figure 6A:
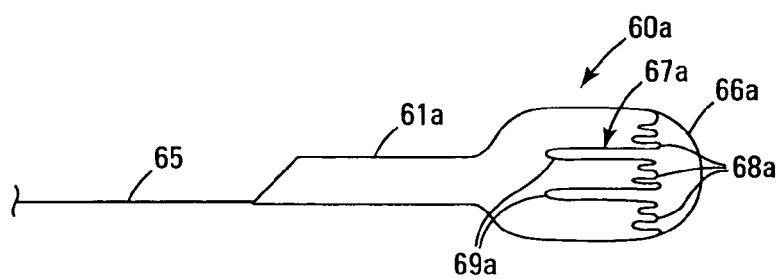
FIG. 6A is a side view of an embodiment of the device of this invention having a delayed expansion feature.
Figure 6B:
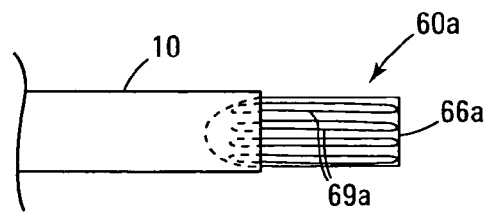
FIGS. 6B and 6C are detail side views showing deployment of the guide seal of FIG. 6A from the distal end of the guide catheter.
Figure 6C:
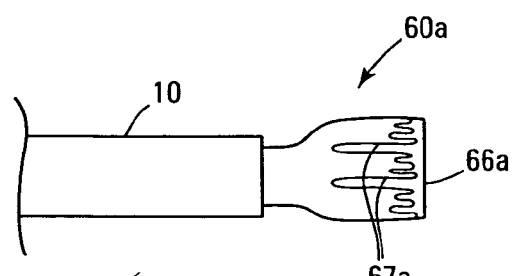
Figure 6D:
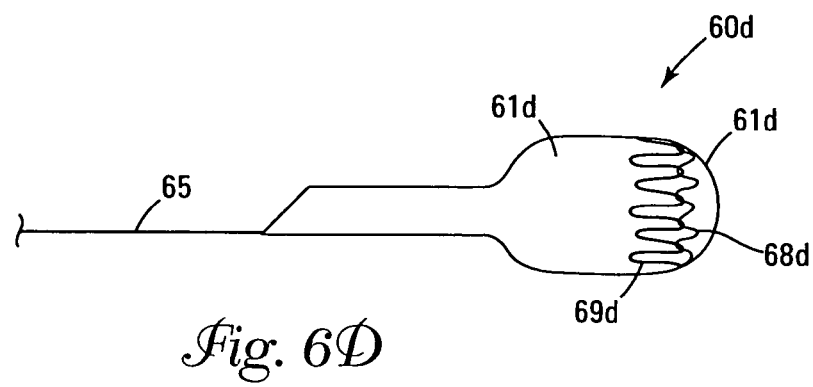
FIGS. 6D to 6F are side views of alternative embodiments of the device of this invention having a delayed expansion feature.
Figure 6E:
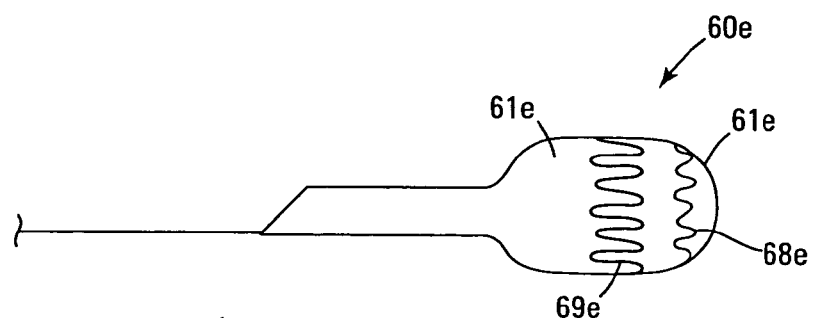
Figure 6F:
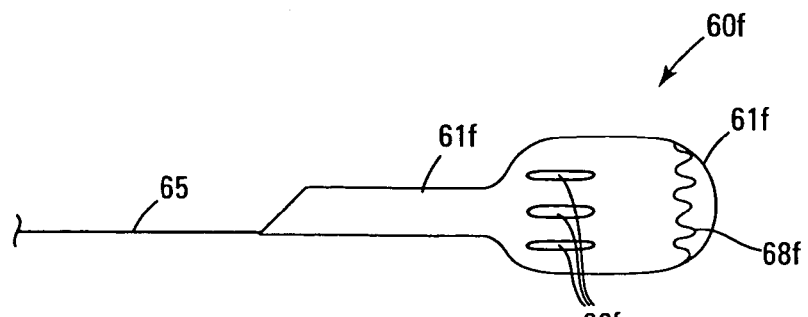

FIGS. 6A to 6C illustrate one embodiment of the guide seal that controls expansion, and other embodiments are shown in FIGS. 6D to 6F. In each embodiment, a guide seal is shown attached to a proximal control wire (65). The wires are embedded in, and can be seen through, polymeric membrane 61a. FIGS. 6A to 6C illustrate that the distal end of the seal comprises expansion wire 67a which includes distal spring sections 68a and longitudinal restraining sections 69a. This expansion wire may be laser cut or etched from a nitinol tube and then heat set into the desired expanded geometry. Alternatively, a frame can be wound from a nitinol wire over a mandrel with radial pins at bends in the wire. The frame is then heat set in the desired expanded geometry. FIG. 6A shows a deployed seal 60a. FIG. 6B illustrates the deployment of guide seal 60a which is shown extending partway out of guide catheter 10. Longitudinal restraining sections 69a serve to resist expansion of the guide seal caused by the expansion of spring sections 68a because they remain constrained within the lumen of the guide catheter until the distal sealing portion has been sufficiently advanced as shown in FIG. 6C.

FIG. 6D illustrates an alternative construction wherein the expansion wire includes flexible spring wire 68d and separate longitudinal restraining wire 69d. Wire 69d is firmer than wire 68d and helps to control expansion in the same manner as described with respect to FIG. 6A. The wires are embedded in polymeric membrane 61d. Similarly, FIG. 6E has a relatively stiff longitudinal restraining wire 69e and a flexible spring wire 68e which together cooperate for a controlled expansion of the guide seal. FIG. 6F illustrates a guide seal 60f similar to that of FIG. 6E but having flat wire ribbons 69f along with flexible spring wire 68f. These various expansion wires may be embedded in the polymer material which forms the distal portion of the guide seal or are otherwise affixed in a conventional manner to such material using adhesives, heat bonding, and the like.

One of skill in the art recognizes that many different shapes, compositions, and diameters of wires and ribbons can be used to obtain the desired effect, which is greater control over the expansion of the distal end of the guide seal into the ostium.

Figure 7A:
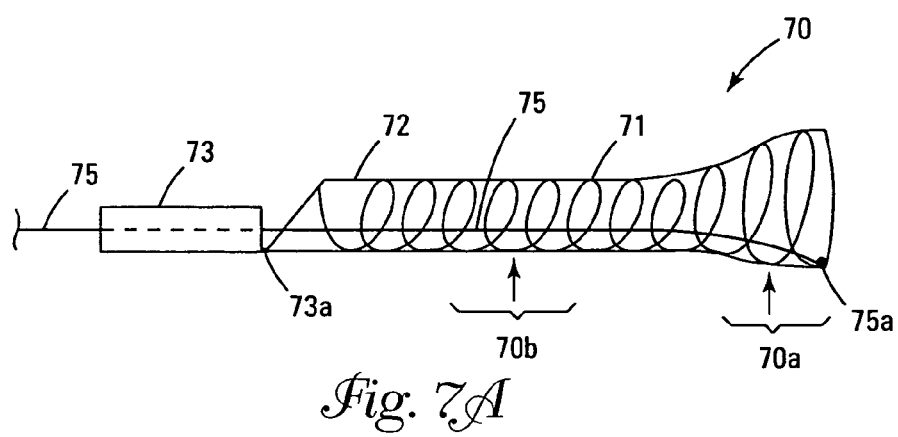
FIG. 7A is a side view of an alternate embodiment of the device of this invention connected to a tube at its proximal end and to a control wire at its distal end.
Figure 7B:
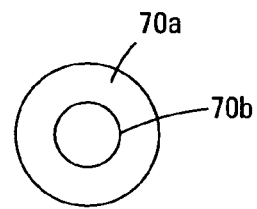
FIGS. 7B and 7C are end views illustrating the relative position of portions of the guide seal.
Figure 7C:
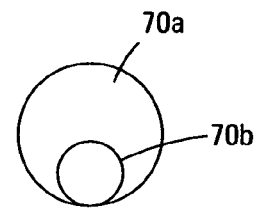

FIGS. 7A to 7C illustrates guide seal 70 having a coil structure instead of a braided wire structure. Coil 71 is covered with an impermeable polymer membrane 72. Because of the coil structure, the guide seal may not be sufficiently rigid to be pushed through the lumen of the guide catheter with a proximally attached control wire. Thus, control wire 75 is connected to the distal end of guide seal 70 at point 75a, either to coil wire 71 or to polymer membrane 72 using methods as described above for FIG. 3A. Tube 73 is connected to the proximal end of guide seal 70 at attachment point 73a either to coil wire 71 or to polymer membrane 72 using methods similar to those described above for wire 35c in FIGS. 3C and 3D. During use the guide seal is advanced distally by advancing control wire 75, which extends out of the proximal end of the guide catheter, in a distal direction. The guide seal is withdrawn by pulling tube 73, which also extends out of the proximal end of the guide catheter, in a proximal direction. FIGS. 7B and 7C are end views that illustrate the relative arrangement of vessel sealing portion 70a and guide catheter sealing portion 70b of guide seal 70. In FIG. 7B, for example, they are coaxial while in FIG. 7C they are axially offset. The offset design is more particularly suited to the structure shown in FIG. 7A, while the structures shown in FIGS. 4, 5, and 6 preferably are coaxial.

Figure 8:
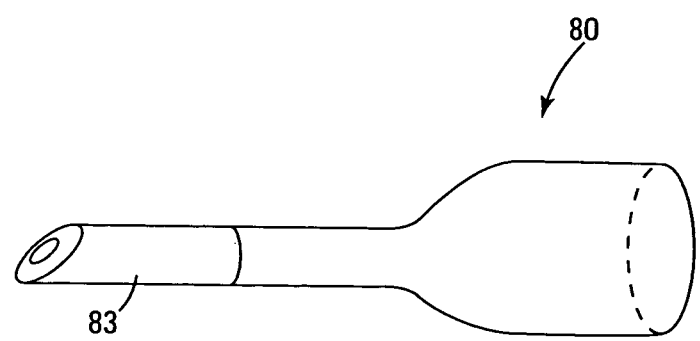
FIGS. 8 and 9 are perspective views of further alternate embodiments of the device of this invention.

FIG. 8 shows an alternate embodiment of the guide seal in which no control wire is used. In this embodiment the guide seal is delivered by using a balloon catheter (not shown). A proximal portion 83 of guide seal 80 is of relatively firm construction that will not expand. An embolic protection device shaft is backloaded through the guide seal into or beside a balloon catheter. The balloon catheter is inserted in the lumen of the guide seal and the balloon is partially inflated to engage the guide seal within portion 83.

Then the balloon catheter/embolic protection device/guide seal combination is loaded into the guide catheter and advanced together down the guide catheter until the guide seal is deployed out the distal end of the guide catheter. The embolic protection device is now advanced distal to the lesion under no-flow or retrograde flow conditions. Then the balloon is deflated and advanced to dilate the lesion while flow has been stopped by the guide seal. Next the balloon is moved proximally and inflated in the lumen of portion 83 of the guide seal to engage the guide seal. The balloon and the guide seal can then be removed together from the guide catheter. Flow is now re-established and emboli carried by the flow into the filter. The filter can now be recovered.

Figure 9:
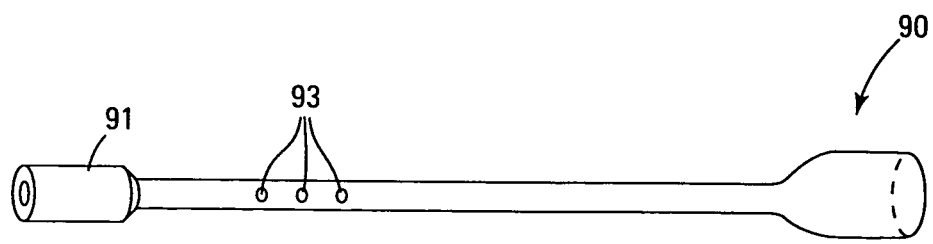

FIG. 9 shows another embodiment in which no control wire is used. Instead, guide seal 90 comprises an elongate tube which extends proximally outside the body to luer lock hub 91. Guide seal 90 is provided with contrast fluid ports 93 which allow contrast fluid to flow through the lumen of the guide seal and exit out the distal end of the guide seal. These ports facilitate fluoroscopic visualization during injection of contrast through the sidearm of the Y connector.

Figure 10A:
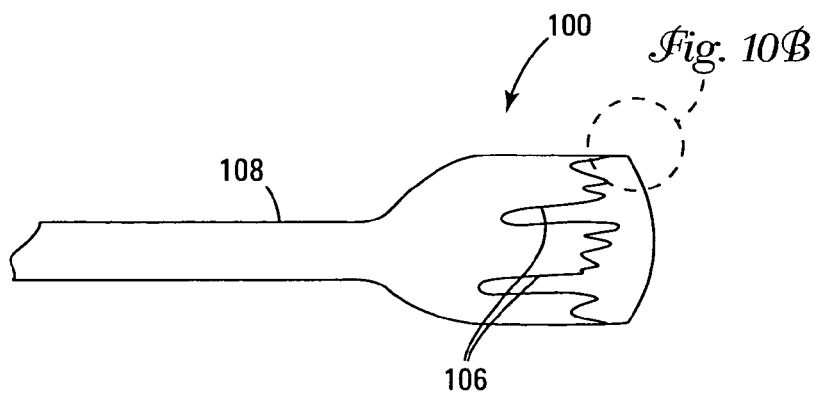
FIG. 10A is a side view of an alternate embodiment of the device of this invention and FIG. 10B is a detail view showing attachment of polymeric membrane to the guide seal frame wire.
Figure 10B:
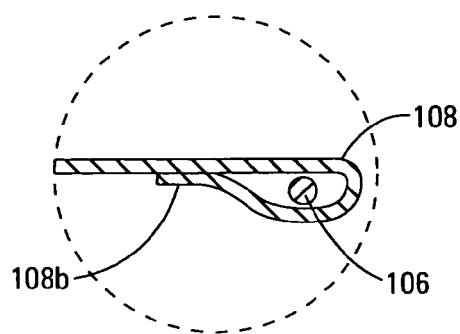

FIG. 10A shows a guide seal 100. A control wire is not shown but would attach at the proximal end. FIG. 10B is a detail cross sectional view of the attachment of polymeric membrane 108 around wire frame 106. The polymer is folded onto itself and fused at region 108b. It could be spot fused or fused continuously around the diameter of the distal end of guide seal 100. In this embodiment, the polymer membrane wraps around the expansion wire at the distal end of the guide seal. This serves to protect the vessel from the wire and to ensure that the wire will not cause a distal protection device to catch on it if the device is exchanged for another.

FIGS. 11 and 12 illustrate different delivery and retrieval control configurations for use with the guide seal of the present invention.

Figure 11A:
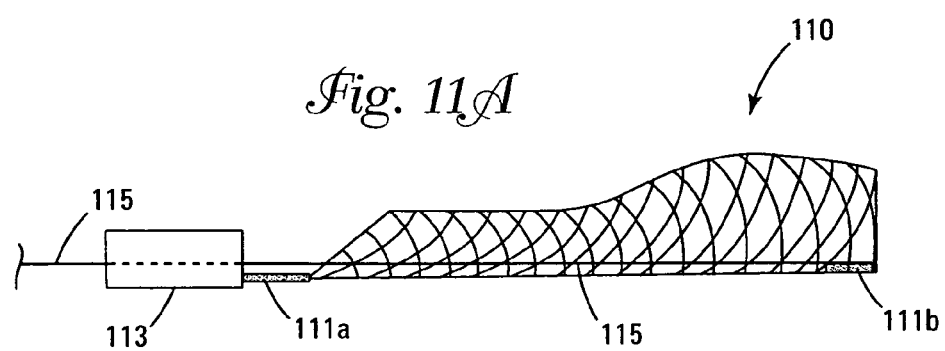
FIG. 11A shows a side view of another embodiment of the device of this invention and FIG. 11B shows a perspective view of a hypotube attached to the guide seal.
Figure 11B:
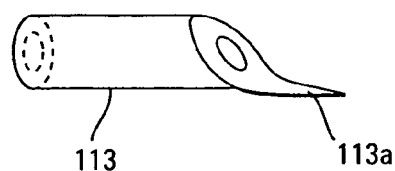

FIG. 11A shows guide seal 110 having control wire 115 that extends proximally through control hypotube 113. Guide seal 110 comprises dense braided metal wire. Dense braided metal wire has a very high pick count, little space between the braid wires when the guide seal is deployed, and is dense enough to effectively stop flow without use of a membrane over the braid. Flow reductions of 95% or greater should satisfy the aims of this invention. Proximal crimp band 111a is used to crimp proximal wires from the braid of the guide seal as well as to attach tab 113a (FIG. 11B) extending from the hypotube. Distal crimp band 111b is used to attach the distal end of the guide seal braid and the distal end of control wire 115. FIG. 11B is a detail view of control hypotube 113, and shows tab 113a at its distal end. Control of the guide seal during delivery and withdrawal is similar to that described with respect to FIG. 7A.

Figure 12A:
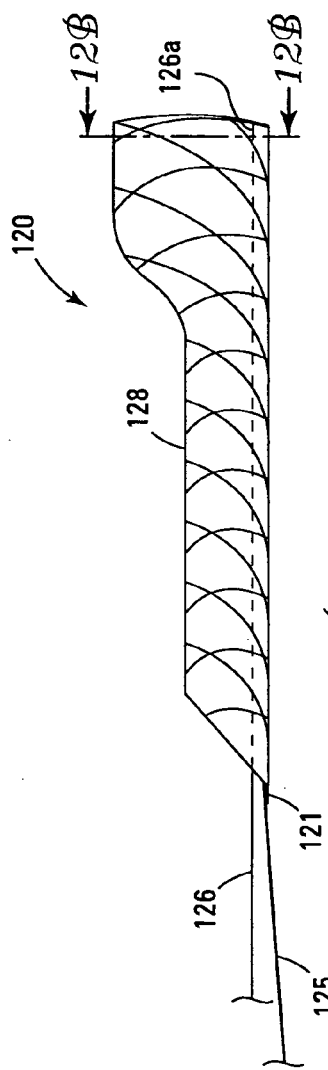
FIG. 12A is a side view of a further alternate embodiment of the device of this invention having two control wires and FIG. 12B is a cross sectional view along line 12B–12B of FIG. 12A showing the distal connection of a control wire.
Figure 12B:
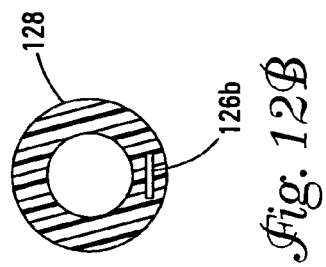

FIG. 12A also illustrates a guide seal comprising braided metal wire. First control wire 125 extends from the proximal end of guide seal 120 and second control wire 126 extends the length of guide seal 120. Proximal crimp band 121 attaches control wire 125 to the proximal end of the guide seal. A distal crimp band could be used to attach control wire 126 to the distal end of guide seal 120, however, in this embodiment, the distal end 126a of control wire 126 is fused into polymer membrane 128 at region 126b, as shown in cross section in FIG. 12B. This typically is done most effectively if the end of the control wire is flattened and then fused into the polymer. Control of the guide seal during delivery and withdrawal is similar to that described with respect to FIG. 7A except control wire 125 is used to withdraw the guide seal.

Figure 13A:
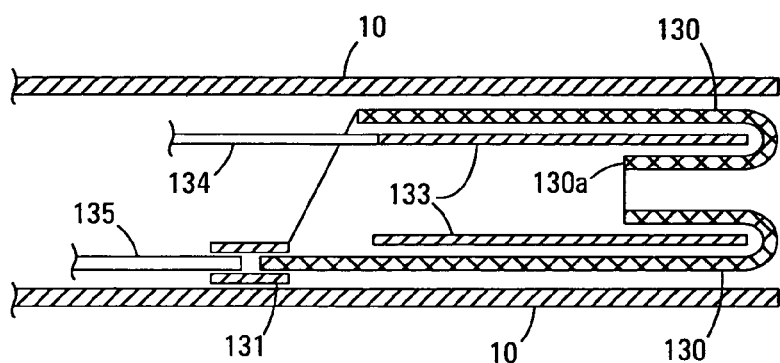
FIGS. 13A and 13B are cross sectional views of an alternative embodiment of the device of this invention having an everting guide seal.
Figure 13B:
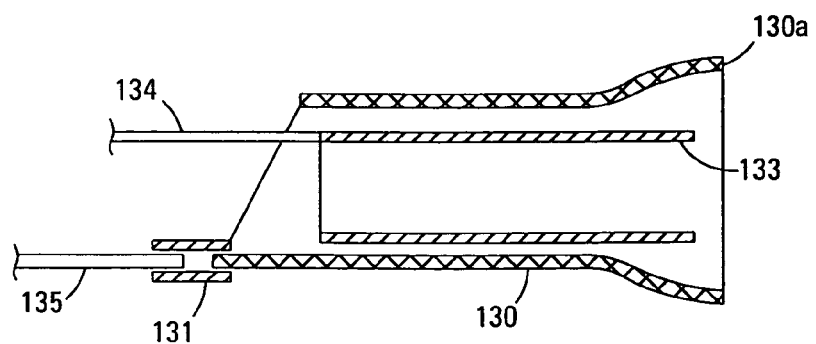

FIGS. 13A and 13B illustrate an everting embodiment of the guide seal. In this embodiment, the braided wire of the guide seal is covered with a lubricious membrane (not shown) so that the guide seal can slide over itself. Guide seal 130 is within guide catheter 10. The distal end 130a of guide seal 130 is folded inside itself and is pushed out, or everted, to elongate the guide seal and deploy the vessel sealing portion. Pusher tube 133 is operably connected to control wire 134 and is urged forward to push the guide seal out the distal end of the guide catheter. Control wire 135 is attached to the proximal end of the guide seal via crimp tube 131. FIG. 13B shows that the pusher tube has advanced the braid of the guide seal out of the distal end of the guide catheter. The everted section expands at the distal end, thus forming the desired seal with the vasculature. The guide seal is withdrawn by withdrawing control wire 135 in a proximal direction.

Figure 14A:
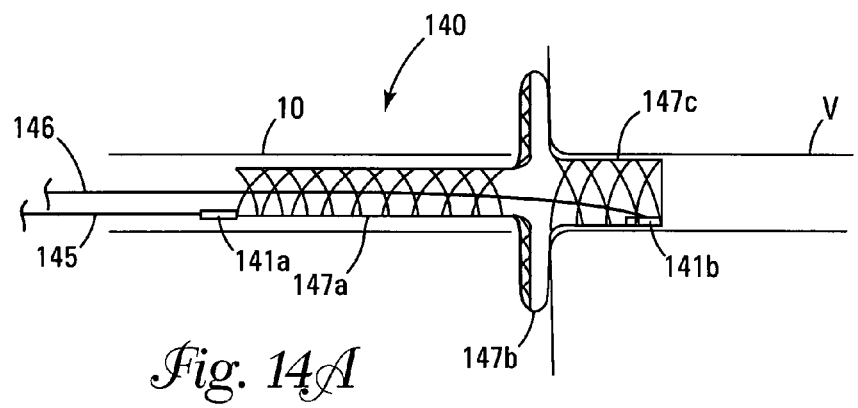
FIG. 14A is a side view of an alternative embodiment of the device of this invention having a disc-shaped guide seal placed in the ostium of a vein.
Figure 14B:
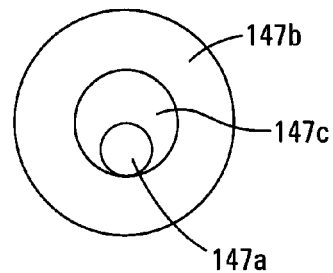
FIG. 14B is a end view showing the relative sizes of portions of the guide seal.
Figure 14C:
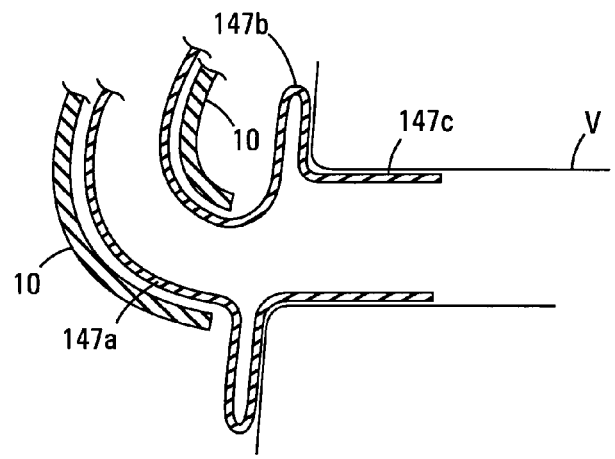
FIG. 14C is a cross-sectional view showing the guide seal and catheter placement relative to the ostium of a vein.

FIG. 14A shows a further embodiment of the guide seal. Guide seal 140 having a disc-shaped portion 147b is shown at the end of guide catheter 10 deployed within saphenous vein graft V. This embodiment is useful in situations where the lesion is close to the ostium of the vessel and there is insufficient room to seat the distal end of the guide catheter in the ostium. Proximal control wire 145 attaches to the proximal end of the guide seal via crimp tube 141a and second control wire 146 extends to the distal end of the guide seal and is attached there via crimp band 141b. Disc-shaped portion 147b seals against the opening of the vessel, and vessel sealing portion 147c seals within the vessel. Proximal portion 147a has a smaller diameter than either portion 147b or 147c. FIG. 14C shows a detail view of deployment of guide seal 140. Control wires are not shown in FIG. 14C for clarity of illustration. The disc-shaped portion 147b forms a seal against the ostium of the saphenous vein graft and against the wall of the aorta. The relative sizes of various portions of the guide seal are shown in FIG. 14B, where disc-shaped portion 147b is larger than vessel sealing portion 147c and proximal portion 147a.

Figure 15:
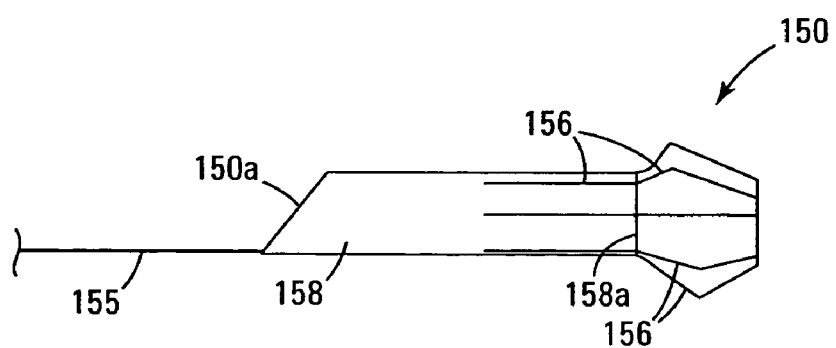
FIG. 15 is a side view of an alternate embodiment of the device of this invention.

FIG. 15 shows yet another embodiment of the guide seal of this invention. Guide seal 150 is formed from heat-set nitinol wires 156 and an elastomeric membrane 158 is disposed over the wires. Fold 158a in the membrane occurs because of the shape of the wires. The nitinol expands into the desired shape when unconstrained (i.e., when it exits the guide catheter). Control wire 155 is embedded in the wall of the guide seal and extends distally through the guide seal to the distal end. Thus the control wire has a heat set bend in it near the distal end of the guide seal. Proximal end 150a of the guide seal has a bias cut. The guide seal fits slidingly within the guide catheter and thus can seal the inside of the guide catheter. To use guide seal 150, it is front loaded into Y connector 7 (as shown in FIG. 1A) using introducer 6 (as shown in FIG. 1D). Preferably, the outer surface of the guide seal is lubricious so that it will advance through the guide catheter without binding.

Figure 16A:
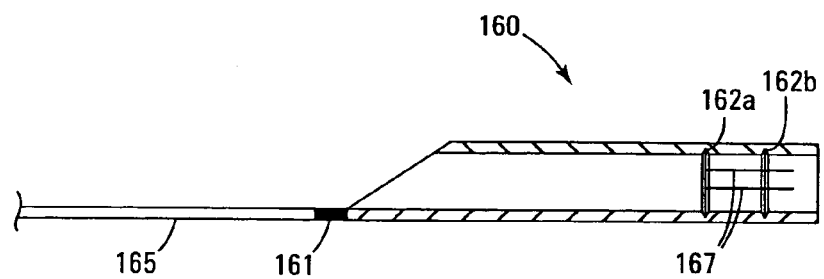
FIG. 16A is a cut away view and FIGS. 16B and 16C are cross sectional views of an alternate embodiment of the device of this invention.
Figure 16B:
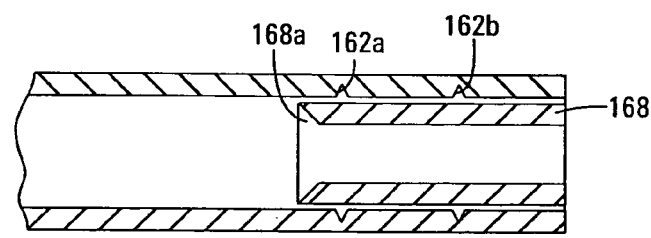
Figure 16C:
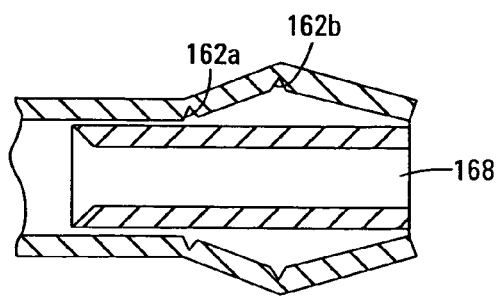

FIGS. 16A to 16C illustrate another embodiment of the device of this invention. Guide seal 160 is attached to proximal control wire 165 at crimp 161. FIG. 16A is a cut away view and FIG. 16B is a cross sectional view that shows guide seal 160 having two grooves 162a and 162b around the inner circumference. These grooves allow the guide seal to bend or flex. Multiple axial slits 167 (two are shown) are provided, which, in conjunction with the grooves, permit the end of the tube to expand. Elastomeric membrane 168 is bonded at each of its ends to the guide seal 160. Elastomeric membrane 168 is chamfered at its proximal end 168a to facilitate passage of other devices. The membrane can be attached using heat, adhesives, or other methods known to one of skill in the art. The membrane is preferably lubricious to facilitate passage of interventional devices. It is attached under tension so that even at rest, membrane 168 provides a restoring force to obtain the desired expanded shape (such as illustrated in FIG. 16C). FIG. 16C, which shows the expanded shape of the guide seal, also illustrates that elastomeric membrane 168 defines a lumen 168c. Importantly, this lumen will prevent passage of devices, such as guidewires, through slits 167 where they could become entangled. The use of guide seal 160 is similar to that of guide seal 150.

The device and method of this invention is particularly useful during interventional procedures such as in cardiology, radiology, and neuroradiology procedures.

Although particular embodiments of the invention have been disclosed herein in detail, this has been done for the purposes of illustration only, and is not intended to be limiting with respect to the scope of the appended claims. It is contemplated that various substitutions, alterations, and modifications may be made to the embodiments of the invention described herein without departing from the spirit and scope of the invention as defined by the claims.

What is claimed is:

1. A method of performing an intravascular procedure at a treatment site in a vessel of a patient comprising:
   providing a sealing device having proximal and distal ends, a distal sealing portion and a proximal sealing portion and having a lumen extending therethrough;
   introducing a guide catheter into the vessel;
   advancing the guide catheter through the vessel until a distal end of the guide catheter is at a desired location proximal of the treatment site;
   introducing the sealing device into a lumen of the guide catheter;
   advancing the sealing device through the lumen of the guide catheter until the distal sealing portion extends from the distal end of the guide catheter;
   occluding the flow of blood through the vessel with the sealing device;
   after blood flow has been occluded advancing a distal protection device through the lumens of the guide catheter and the sealing device and through the vessel to a location distal to the treatment site;
   deploying the distal protection device;
   after the distal protection device has been deployed withdrawing the distal sealing portion of the sealing device into the guide catheter to thereby re-establish the antegrade flow of blood though the vessel at the treatment site;
   advancing a vascular treatment device through the guide catheter to the treatment site and performing the intravascular procedure with the treatment device while blood is flowing antegrade through the vessel at the treatment site.

2. The method of claim 1 wherein in the step of providing a sealing device the distal sealing portion is expandable from a delivery configuration to a deployed configuration.

3. The method of claim 1 wherein in the step of providing a sealing device the proximal sealing portion has a first diameter and the distal sealing portion has a second diameter when extended from the distal end of the guide catheter, the second diameter being larger that the first diameter.

4. The method of claim 1 wherein in the step of providing a sealing device the sealing device comprises metal wire.

5. The method of claim 4 wherein in the step of providing a sealing device the metal wire comprises nitinol.

6. The method of claim 1 wherein in the step of providing a sealing device the sealing device further comprises a control element connected adjacent at least one of the distal and proximal ends of the sealing device.

7. The method of claim 6 wherein the control element comprises a control wire.

8. The method of claim 6 wherein the control element comprises a tube.

9. The method of claim 6 wherein the control element comprises an elongate proximal portion of the sealing device having a length sufficient to extend outside the patient during advancement of the sealing device.

10. The method of claim 1 wherein in the step of providing a sealing device the sealing device comprises a flexible membrane.

11. The method of claim 1 wherein in the step of providing a sealing element the distal sealing portion comprises a flexible membrane which is folded into the lumen of the sealing device, wherein the sealing device further includes a deployment member, and wherein the step of occluding the flow of blood comprises advancing the deployment member through the lumen of the sealing device to push the folded membrane out of the lumen of the sealing device.

12. The method of claim 1 wherein in the step of providing a sealing device the sealing device comprises at least one flow window between the lumen of the sealing device and an exterior surface of the sealing device.

13. The method of claim 1 wherein in the step of providing a sealing device the distal sealing portion is expandable from a delivery configuration to a deployed configuration and wherein the sealing device includes means to delay expansion of the distal sealing portion.

14. The method of claim 13 wherein the delay means includes longitudinal restraining elements positioned adjacent the distal sealing portion.

15. The method of claim 1 wherein the step of advancing the sealing device comprises inflating a balloon portion of a balloon catheter in the lumen of the sealing device until the sealing device is secured to the balloon catheter and then advancing the balloon catheter through the lumen of the guide catheter.

16. The method of claim 1 wherein in the step of providing a sealing device the sealing device includes means to bias the proximal sealing portion outwardly to seal against the lumen of the guide catheter.

17. The method of claim 16 wherein the biasing means comprises a spring wire.

18. The method of claim 16 wherein the biasing means comprises open cell foam.

19. The method of claim 16 wherein the biasing means comprises a locally thinned portion of the proximal sealing portion.

20. The method of claim 1 wherein the treatment site is located adjacent an ostium of the vessel and wherein in the step of providing a sealing device the distal sealing portion has a first section with a first diameter sized to seal the vessel proximal to the ostium and a second section with a second larger diameter.

21. A method of performing an intravascular procedure at a treatment site in a vessel of a patient comprising:
providing a sealing device having proximal and distal ends, a distal sealing portion and a proximal sealing portion and having a lumen extending therethrough;
introducing a guide catheter into the vessel, the guide catheter having proximal and distal ends and a lumen and a valve connected at the proximal end for opening and closing the lumen of the guide catheter to fluid flow;
advancing the guide catheter through the vessel until the distal end of the guide catheter is at a desired location proximal of the treatment site;
introducing the sealing device into the lumen of the guide catheter;
advancing the sealing device through the lumen of the guide catheter until the distal sealing portion extends from the distal end of the guide catheter;
blocking antegrade blood flow through the vessel with the sealing device;
opening the valve on the guide catheter to create retrograde blood flow through the vessel;
after antegrade blood flow has been blocked advancing a distal protection device through the lumens of the guide catheter and the sealing device and through the vessel to a location distal to the treatment site;
deploying the distal protection device;
after the distal protection device has been deployed withdrawing the distal sealing portion of the sealing device into the guide catheter to thereby re-establish the antegrade flow of blood through the vessel at the treatment site;
advancing a vascular treatment device through the guide catheter to the treatment site and performing the intravascular procedure with the treatment device while blood is flowing antegrade through the vessel at the treatment site.

22. A method of performing an intravascular procedure at a treatment site in a vessel of a patient comprising:
providing a sealing device having proximal and distal ends, a distal sealing portion and a proximal sealing portion and having a lumen extending therethrough;
introducing a guide catheter into the vessel, the guide catheter having proximal and distal ends and a lumen and a suction device connected to the lumen;
advancing the guide catheter through the vessel until the distal end of the guide catheter is at a desired location proximal of the treatment site;
introducing the sealing device into the lumen of the guide catheter;
advancing the sealing device through the lumen of the guide catheter until the distal sealing portion extends from the distal end of the guide catheter;
blocking antegrade blood flow though the vessel with the sealing device;
operating the suction device to create retrograde blood flow through the vessel;
after antegrade blood flow has been blocked advancing a distal protection device through the lumens of the guide catheter and the sealing device and through the vessel to a location distal to the treatment site;
deploying the distal protection device;
after the distal protection device has been deployed withdrawing the distal sealing portion of the sealing device into the guide catheter to thereby re-establish the antegrade flow of blood through the vessel at the treatment site;
advancing a vascular treatment device through the guide catheter to the treatment site and performing the intravascular procedure with the treatment device while blood is flowing antegrade through the vessel at the treatment site.

* * * * *